United States Patent
Athanasiou et al.

(10) Patent No.: US 10,527,574 B2
(45) Date of Patent: Jan. 7, 2020

(54) BIOSENSOR DEVICE AND SYSTEM

(71) Applicant: DNAE GROUP HOLDINGS LIMITED, London (GB)

(72) Inventors: Panteleimon Athanasiou, London (GB); Alpesh Patel, London (GB); David Whitaker, London (GB); Hua Bai, Harsoton (GB); John Palmer-Felgate, Horsham (GB); Daniel Coomber-Alford, London (GB); Jessica Fisher, London (GB); Chad Schneider, London (GB); Alex Flamm, Baltimore, MD (US); Ben Lane, Hydes, MD (US); Samuel Reed, London (GB)

(73) Assignee: DNAE GROUP HOLDINGS LIMITED, London (GB)

(*) Notice: Subject to any disclaimer, the term of this patent is extended or adjusted under 35 U.S.C. 154(b) by 0 days.

(21) Appl. No.: 15/394,909

(22) Filed: Dec. 30, 2016

(65) Prior Publication Data
US 2017/0106371 A1 Apr. 20, 2017

Related U.S. Application Data

(63) Continuation of application No. 14/387,354, filed as application No. PCT/GB2013/050832 on Mar. 28, 2013, now Pat. No. 9,739,743.

(30) Foreign Application Priority Data

Mar. 28, 2012 (GB) .................................. 1205497.9

(51) Int. Cl.
*G01N 27/327* (2006.01)
*B01L 3/00* (2006.01)
(Continued)

(52) U.S. Cl.
CPC .......... *G01N 27/327* (2013.01); *B01F 5/065* (2013.01); *B01F 5/0647* (2013.01);
(Continued)

(58) Field of Classification Search
None
See application file for complete search history.

(56) References Cited

U.S. PATENT DOCUMENTS

| 3,837,534 A | 9/1974 | Natelson |
| 4,246,339 A | 1/1981 | Cole et al. |

(Continued)

FOREIGN PATENT DOCUMENTS

| DE | 10238600 A1 | 3/2004 |
| DE | 102011001550 A1 | 9/2012 |

(Continued)

OTHER PUBLICATIONS

International Search Report and Written Opinion dated Jan. 2, 2014 from corresponding International Patent Application No. PCT/GB2013/050832, 16 pgs.; Search Report under Section 17 from the priority document of GB Application No. GB1205497.9; 2 pgs.

(Continued)

*Primary Examiner* — Matthew D Krcha
(74) *Attorney, Agent, or Firm* — Maier & Maier, PLLC

(57) ABSTRACT

A system, device, and method for receiving, preparing and identifying a biological sample. Some parts may be user held and actuated. The sample may be detected by an array of sensors. The system may comprise reusable and disposable components arranged to be connected together. The biological sample may contain nucleic acids, proteins, or other molecules to be detected.

3 Claims, 22 Drawing Sheets

(51) Int. Cl.
*B01F 5/06* (2006.01)
*B01F 13/00* (2006.01)
*B01L 7/00* (2006.01)
*G01N 27/414* (2006.01)

(52) U.S. Cl.
CPC .......... *B01F 13/0059* (2013.01); *B01L 3/502* (2013.01); *B01L 3/5025* (2013.01); *B01L 3/5029* (2013.01); *B01L 3/50851* (2013.01); *B01L 3/50853* (2013.01); *B01L 3/502715* (2013.01); *B01L 3/502723* (2013.01); *B01L 3/502738* (2013.01); *B01L 7/52* (2013.01); *G01N 27/4145* (2013.01); *G01N 27/4148* (2013.01); *B01F 2215/0037* (2013.01); *B01F 2215/0431* (2013.01); *B01L 2200/0684* (2013.01); *B01L 2200/0689* (2013.01); *B01L 2200/16* (2013.01); *B01L 2300/048* (2013.01); *B01L 2300/0609* (2013.01); *B01L 2300/0636* (2013.01); *B01L 2300/0645* (2013.01); *B01L 2300/0819* (2013.01); *B01L 2300/0867* (2013.01); *B01L 2300/0883* (2013.01); *B01L 2300/1827* (2013.01); *B01L 2400/0478* (2013.01); *B01L 2400/0638* (2013.01); *B01L 2400/0677* (2013.01)

(56) References Cited

U.S. PATENT DOCUMENTS

| | | | |
|---|---|---|---|
| 4,753,536 A | 6/1988 | Spehar et al. | |
| 5,726,026 A * | 3/1998 | Wilding | B01D 67/0062 366/DIG. 3 |
| 5,839,467 A | 11/1998 | Saaski et al. | |
| 6,656,428 B1 * | 12/2003 | Clark | B01L 3/502 422/404 |
| 7,851,207 B1 | 12/2010 | Sagripanti | |
| 2002/0151776 A1 | 10/2002 | Shawgo et al. | |
| 2004/0033168 A1 | 2/2004 | Hughes | |
| 2004/0065655 A1 | 5/2004 | Brown et al. | |
| 2004/0208792 A1 | 10/2004 | Linton et al. | |
| 2005/0186121 A1 | 2/2005 | West | |
| 2005/0119589 A1 * | 6/2005 | Tung | A61B 10/0045 600/584 |
| 2005/0214928 A1 | 9/2005 | Larsen | |
| 2007/0031297 A1 | 2/2007 | Roussel | |
| 2011/0244466 A1 * | 10/2011 | Juncosa | B01L 3/502 435/6.12 |
| 2012/0328488 A1 * | 12/2012 | Puntambekar | B01L 3/5025 422/503 |

FOREIGN PATENT DOCUMENTS

| | | | | |
|---|---|---|---|---|
| EP | 2233210 A1 | 9/2010 | | |
| WO | 97/24529 A2 | 7/1997 | | |
| WO | 01/11374 A2 | 2/2001 | | |
| WO | 02/087762 A1 | 11/2002 | | |
| WO | 2004/065010 A2 | 8/2004 | | |
| WO | 2010/125404 A1 | 11/2010 | | |
| WO | WO-2010125404 A1 * | 11/2010 | | B01L 3/502 |
| WO | 2012072822 A1 | 6/2012 | | |

OTHER PUBLICATIONS

Extended European Search Report dated Apr. 24, 2018, including the European Search Report and the European Search Opinion, in connection with corresponding EP Application No. 17210118.0 (7 pgs.).

Japanese Office Action dated May 1, 2018, in connection with corresponding JP Application No. 2017-092052 (8 pgs., including English translation).

* cited by examiner

BIOSENSOR DEVICE AND SYSTEM

FIELD OF THE INVENTION

The present invention relates to a method, device and system for handling a fluid sample to be tested with a biosensor. The invention is particularly relevant for animal bodily fluid and plant samples for use in nucleic acid testing and diagnosis.

BACKGROUND

Testing biological samples is typically a multi-step process performed in a laboratory by skilled technicians. The following workflow considers a DNA test for a human patient. The biological sample must be first taken from the donor using a swab or collection vial. The swab for wiping over buccal tissue is an open-celled foam which traps the donor cells within the foam cells. The foam is then immersed and agitated in a fluid to release the biological cells. A series of reagents* are added to (a) break the cells open and release DNA; (b) purify the released DNA and (c) mixed the DNA with reagents for amplification (pH, buffering, stabilizing agents, polymerase, primers, probes, beads, nucleotides, etc). These reagents are added either by hand pipetting or in an automated process for batch testing. At some point it is desirable to separate out unwanted particulate (food, cell debris, etc). This can be by a mechanical sieve or by centrifuge. The DNA may then be tested using known techniques such as Sanger sequencing, Sequencing by Synthesis, or real time PCR.

The entire process is quite complex and requires skilled persons using expensive equipment to provide a result, which typically takes hours to days to return to the person requesting the test.

The inventors appreciated that it is desirable to replace the above system of testing with a simple, inexpensive device not requiring specialist skills to operate or interpret. They have thus devised a device described below which can be hand operated by the lay user.

SUMMARY OF THE INVENTION

According to a first aspect of the invention there is provided a biological sample preparation device comprising: a housing; a plurality of fluid dispensers located within the housing; a user actuated member coupled to the housing and movable relative to the housing; and a mechanism to translate movement of the member into a preset combination of sequential and simultaneous movements of the fluid dispensers, in order to mix the sample and reagents.

The mechanism may be provided by one or more cams coupled to the member and a plurality of followers, one follower coupled to each fluid dispenser, arranged such that movement of the member relative to the housing causes the one or more cams to act upon the followers to dispense a fluid from said fluid dispensers.

The member may be arranged to rotate relative to the housing.

Each fluid dispenser may comprise a plunger and a cylinder adapted to receive said plunger at one end and dispense fluid through a port in the other end.

An end of each plunger may be acted upon by one of the one or more cams.

The member may comprise a surface texture arranged to increase gripping.

[Col. 2]

The member may comprise a plurality of concentric cams tracks, preferably the cam tracks provide a dwell portion, displacement portion, and locked portion to each dispenser.

The device may comprise a ratchet between the housing and member.

According to a second aspect of the invention there is provided a biological sample preparation device comprising: at least two fluid dispensers, at least one of which dispensers contains a reagent sealed in that dispenser; a microfluidic channel 62 connecting each of the fluid dispensers to a receiving chamber, wherein the fluid dispensers are arranged to dispense fluid to flow substantially simultaneously through the fluid channel to the receiving chamber.

The receiving chamber may have a bleedhole arranged to expel air and expel fluid in excess of a predetermined volume.

The fluid channel may comprise a serpentine path and/or surface texture to promote mixing between fluids flowing in the channel.

The channel may be an open-sided channel formed in a solid substrate, the open portion of the channel being covered by a layer covering the substrate, preferably by a foil or adhesive film.

The dispensers may each comprise a plunger to act upon the fluid, preferably wherein two or more plungers may be connected together, preferably forming an integrated component.

A mixing ratio may be determined by the volume of fluid dispensed from each fluid dispenser.

At least one dispenser may comprise a sealed cylinder containing a reagent.

The device may be handheld and hand actuated.

The dimensions of the fluid dispenser are chosen to dispense a predetermined amount of fluid, preferably less than 500 ul.

According to a third aspect of the invention there is provided a fluid mixing device, the device comprising: a base defining a) a channel having an open side and b) a fluid port, wherein the port is separated from the channel by a dam; and a membrane attached to the base covering the open side of the channel and the port.

A portion of the membrane may be arranged to move away from the base under hydraulic pressure on the port to allow fluid from the port to flow over the dam and into the channel.

The dam surrounds the port and a void surrounds the dam.

The device may comprise a reservoir in fluidic communication with and located between the port and the channel. The reservoir and an outlet from the reservoir to the channel may be configured such that fluid fills the reservoir before exiting. Such filing of the reservoir ensures that there are no an air pockets created in the reservoir.

According to a fourth aspect of the invention there is provided a device for extracting a biological fluid sample comprising: a first component having a handle and a swab at an end of the handle for absorbing a fluid in an uncompressed state; and a second component having an opening to receive the swab and a chamber arranged to interfere with the swab to compress the swab in an compressed state.

The device may comprise a lid protruding from the handle to substantially cover the opening of the second component when the swab is in the compressed state.

An entry to the chamber is larger than the swab in the uncompressed state and the chamber narrows to receive the compress the swab into a compressed state.

The device may comprise a port on the chamber to allow the fluid sample to exit the chamber.

The device may comprise a locking mechanism formed by cooperating portions of the first and second component to lock the swab into the compressed state, preferably wherein the locking mechanism is a detent.

According to a fifth aspect of the invention there is provided a device for extracting a biological fluid sample comprising: a handle; a swab at an end of the handle for absorbing a fluid; and a collar arranged to slide along the handle to compress the swab.

The collar may have a recess spaced away from the handle to receive the swab into a compressed state.

The swab may be detachable from the handle.

The collar may be slidable between an initial position where the swab is uncompressed and a compressing position where the collar interferes with the swab to expel the fluid therefrom.

The collar may cooperate with an external component via a detent to lock the collar into the compressed position.

The swab comprises a closed-cell foam.

According to a sixth aspect of the invention there is provided a method of sensing a biological property of a sample comprising the steps of: providing a fluid containing the sample to a microfluidic container, each container having a sensor and reagents covered by or fixed in a substance; melting the substance to controllably release the reagents to react with the sample; correlating reagents and an output signal from the sensor in each container to determine a property of the sample.

The reagents may be analyte-specific reagents, preferably allele-specific primers or antigen-specific antibodies, which chemically bind to a target, if present in the sample.

The sensors may be configured to detect one or more by-products of reactions between the reagents and the sample.

The method may comprise the step of covering the plurality of containers to isolate the containers from each other and/or may comprise the step of switching on a heater.

According to a seventh aspect of the invention there is provided a cartridge for sensing biological properties of samples and comprising: a housing; a semiconductor chip having integrated therein an array of sensors; an array of microfluidic wells for receiving the samples; reagent covered by or fixed in a substance located in each wells; and a heater configured to provide heat to the substance.

The substance may have a melting point above ambient temperature and below the operating temperature of the chip, preferably wherein the substance is a wax, more preferably paraffin.

The cartridge may comprise a surface, which is movable to isolate the wells from each other.

The cartridge may comprise a temperature sensor.

The cartridge may comprise a controller coupled to the heater and temperature sensor.

According to an eighth aspect of the invention there is provided a cartridge for sensing biological samples comprising: a housing; a semiconductor chip having integrated therein an array of sensors; a sealing block spaced apart from the chip to form a gap therebetween; an array of wells open on one side to receive the samples, wherein the sealing block and chip are arranged to move relative to one another between an non-sealing position and a sealing position to close the gap so as to isolate the wells from each other.

The cartridge may comprise an actuator arranged to urge the sealing block into the sealing position as the cartridge is removed from an external device.

The cartridge may comprise an array of electrodes exposable to the wells.

The cartridge may comprise biasing means to space the sealing block away from the semiconductor chip in the non-sealing position.

The cartridge may comprise a heat sink connected to the semiconductor chip.

The cartridge may comprise a port in the housing to receive a fluid sample.

The cartridge may comprise a port in the housing to receive and direct airflow to the semiconductor chip and/or a heat sink.

The cartridge may comprise a mechanical connector to connect the cartridge to an external device.

The cartridge may comprise an electrical connector (83) to connect the semiconductor chip to an external circuit.

The gap may be set to provide a capillary force to hold the fluid over the sensors.

The cartridge may comprise comprising a flexible skirt surrounding at least part of the semiconductor chip to contain excess fluid.

The array of microfluidic wells may be provided by openings in a planar substrate, preferably wherein the substrate comprises a printed circuit board (PCB), more preferably a flexible PCB.

The cartridge may comprise a wetting agent coating a surface of the wells.

The volume of each well is preferably greater than 20 nl, more preferably greater than 50 nl, preferably less than 200 nl, more preferably less than 100 nl.

According to a ninth aspect of the invention there is provided a microfluidic device for biological reactions, the device having a laminate structure (116) and comprising: a planar substrate; conductive tracks deposited on a major surface of the planar substrate; an insulating layer covering the conductive tracks and planar substrate; and one or more openings traversing through the laminate structure to provide one or more microfluidic container, wherein tracks are exposed only at an edge to each microfluidic container to provide an electrode.

The microfluidic device may comprise electrical connectors to connect the conductive tracks to an external circuit providing an electrode reference voltage.

The microfluidic device may comprise a circuit providing an electrode reference voltage to the reference electrodes.

The tracks may comprise a plurality of track channels electrically isolated from each other.

Neighbouring microfluidic containers may be exposed to different track channels.

According to a tenth aspect of the invention there is provided a method of manufacturing a microfluidic device comprising the steps of: providing a planar substrate; depositing a first set of conductive tracks on the substrate; covering the track and substrate with a conformal insulating layer; cutting through the layers provided by steps (i) to (iii) to form openings exposed to only an edge of the conductive track.

The laminate may be die cut through the layers

The openings form part of a microfluidic container to receive a fluid.

The method may couple a semiconductor substrate comprising one or more sensors to the layers with a conformal sealing layer The planar substrate may be a PCB The first set of conductive tracks may comprise a noble metal, preferably silver/silver-chloride.

The method may comprise depositing and etching a second set of conductive tracks on the substrate, electrically separated from the first set.

The conductive tracks may be deposited by screen printing

The method may comprise depositing bond pads onto the conductive tracks.

According to an eleventh aspect of the invention there is provided a device for determining biological properties comprising: a housing; a port on the housing having mechanical and electrical coupling means for coupling the device to an external sensor cartridge; and a circuit board within the housing having a controller and signal processing circuit to control the temperature of and process sensor signals from the sensor cartridge via the electrical coupling.

The device may comprise means for connecting the device to an external computer.

The device may comprise a fan arranged to direct air flow through said port to the external sensor cartridge.

According to a twelfth aspect of the invention there is provided a system for testing a biological sample comprising: a sample preparation device for receiving the sample, the sample preparation device having reagents and a mixer to mix said reagents with the sample; a sensor cartridge having one or more sensors, the cartridge being connectable to the sample prep device to receive a mixture of sample and reagents.

The system may comprise one or more of: a swab to take the sample from a donor, an analyser connectable to the cartridge to receive and process output signals from the one or more sensors; and a fluid dispenser containing the reagents.

BRIEF DESCRIPTION OF THE DRAWINGS

Specific embodiments of the invention will now be described by way of example only with reference to the accompanying figures, in which.

DETAILED DESCRIPTION

The system comprises a swab, sample preparation device, sensor cartridge and analyser.

System Overview

Figure 1:
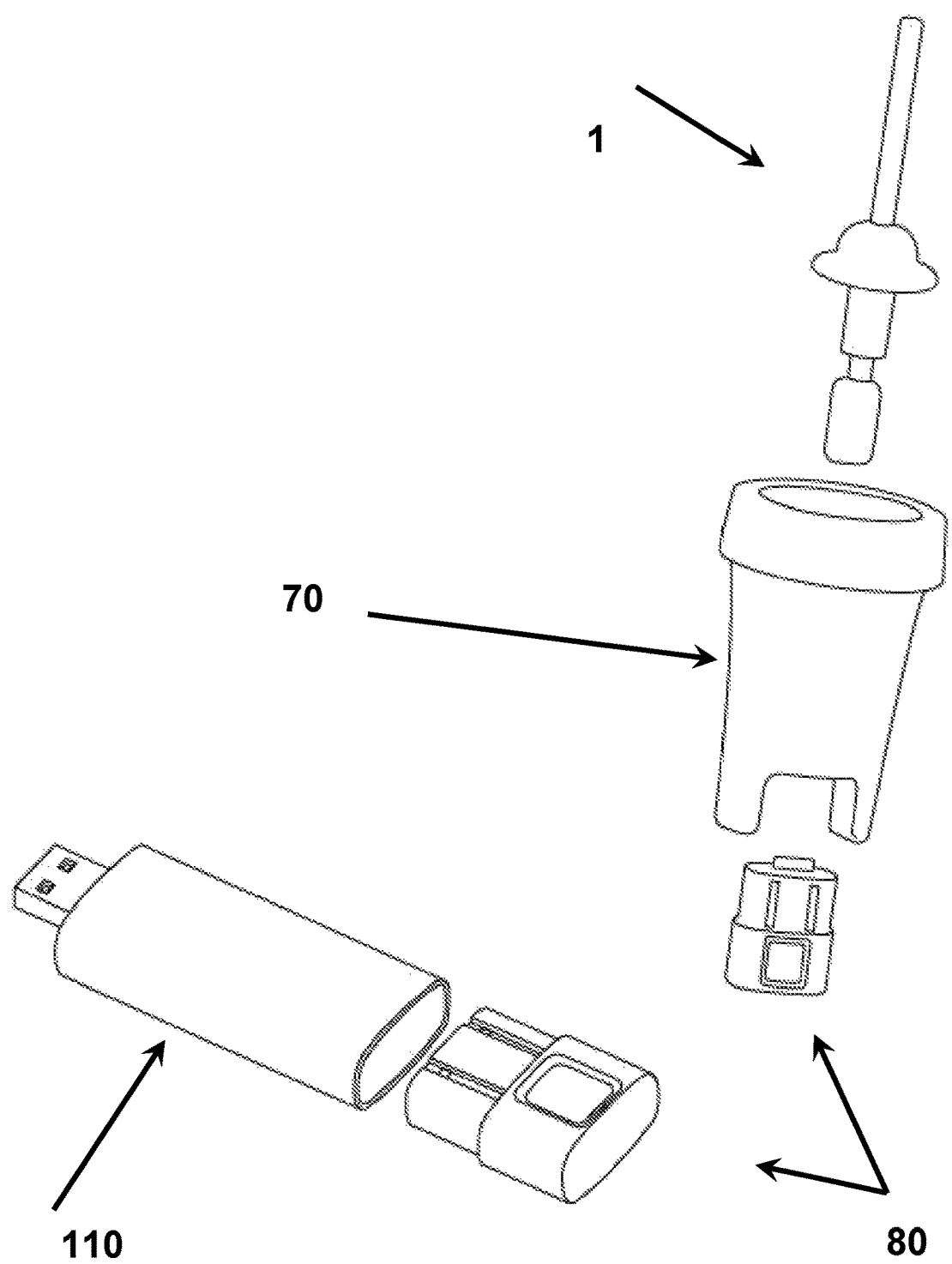
FIG. 1 is an exploded illustration of components of a preferred system.

A system for taking a biological sample is shown in FIG. 1. This exemplary system comprises a swab 1 for taking a sample from an animal (e.g. humans and other mammals, including samples containing pathogens); a sample preparation device 70 for providing the sample in a usable format; a sensor cartridge 80 for detecting properties of the sample; and an analyser 110 for processing the signals of the sensor to provide an output to the user or further connected devices.

The system may be flexible to operate with a variety of sample types, reagents, sensor arrangements, and analysers such that a variety of tests and diagnosis may be obtained from a variety of biological sources. For example, the sample may be one of many bodily fluids containing cells or cells scraped from an organ or infection, which when mixed with the appropriate reagents, provide DNA or RNA in a fluid at usable conditions (concentration, pH, buffer, etc.) to be detected by one or more sensors, preferably an array of sensors, sensitive to one or more properties. Some of the reagents may be analyte specific reagents isolated from each other by microfluidic wells exposed to sensors, to determine the identities of a plurality of nucleic bases of the DNA or RNA. Other specific reagents may also be used to identify samples other than nucleic acids, such as proteins.

Nucleic acids such as DNA or RNA can be isolated from animal tissue or cells, plant tissue or cells, bacterial cells, viral particles or virus infected cells. The sample may be acquired from various sources such as from blood, saliva, faecal, leaf disc or soil. Methods of extracting nucleic acids from unprocessed samples can be adopted depending on the source of the sample and whether a pre-processing step such as mechanical shearing, sonication or filtration of insoluble material is required. The extracted nucleic acids can be used for various downstream applications such as nucleic acid amplification, DNA sequencing or nucleic acid quantification.

Figure 19:
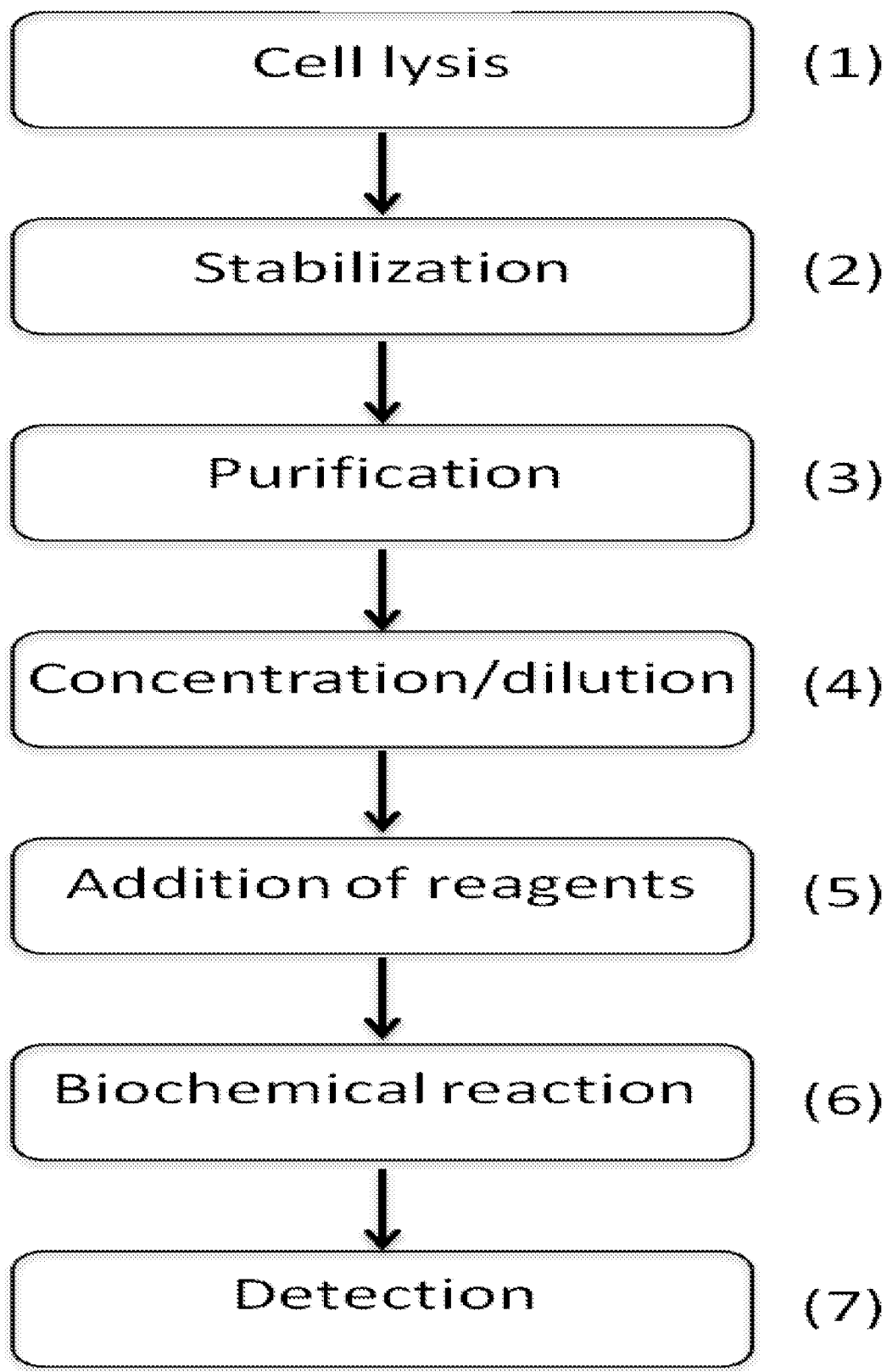
FIG. 19 is a flowchart of steps in extracting and analysing nucleic acids from tissues or cells.

The steps in extracting and analysing nucleic acids from tissues or cells are illustrated in FIG. 19. In certain applications, some of these steps can be combined. The first step requires lysing of tissues or cells using chemical or enzymatic means (1). The optimal lysis is achieved by combining an amount of sample with lysis buffer in an optimal ratio. Next, a stabilizer may be added to the mixture to prevent degradation of the nucleic acids and protect the overall integrity of the nucleic acid (2). Alternatively, the stabilizer, if compatible, may be incorporated into the lysis buffer. Depending on the downstream application, increasing the purity of the nucleic acids mixture by removing non-targeted nucleic acids may be necessary in order to achieve the optimal assay condition for the downstream applications (3). The purity of the nucleic acids mixture can be increased by enzymatic digestion, chelation and/or filtration of unwanted/ interfering substances. The resulting nucleic acid mixture may be further concentrated or diluted (4) and subsequently combined with the appropriate reaction reagents (5) for downstream applications (6) and detection (7).

In one embodiment, other biomolecules, such as proteins, can be isolated and analysed using the steps similar to the method described for the nucleic acid analysis.

The methods and the components of the lysis buffers, stabilizers, purification techniques and reaction reagents will vary depending on the source of the samples, the biomolecules to be analysed (DNA, RNA or protein) and the downstream applications. Those skilled in the art will be able to make modifications and alternatives in view of the disclosure which are considered as falling within the scope of the invention. FIG. 19 shows the steps in extracting and analysing nucleic acids from tissues or cells. The first four steps preferably take place in a sample preparation device and the last two take place in a sensor cartridge.

Below is an example of a method of extracting DNA from human saliva for a genetic diagnostic assay.

An amount of saliva is mixed with an alkaline lysis buffer in a predetermined ratio to achieve the optimal lysis in a favourable pH. The alkaline lysis buffer comprises an alkali base; a metal chelator, such as EDTA; and may include one or more non-ionic detergent, such as Triton-X 100. The alkali base in the alkaline lysis buffer is used to disrupt the cell membrane, denature proteins, as well as to adjust the extracted saliva fluid to obtain an optimal pH for nucleic acid amplification and detection. The preferred pH range of the alkaline lysis buffer is between pH 10-14.

For nucleic acid amplification, such as PCR or isothermal amplification such as TMA, SDA, HDA, RPA, NASBA or LAMP, a specific fraction of the saliva/lysis buffer mixture is combined with amplification reagent solution to facilitate nucleic acid amplification. The amplification reagents solution comprises components necessary for efficient DNA amplification such as dNTPs, polymerase, MgSO4 and NH4Cl; but excluding sequence-specific primers or probes, which are stored in the sensor cartridge.

To initiate the nucleic acid amplification reaction, the saliva-lysis buffer mixture is combined with the amplification reagents, which adjust the final pH, prior to amplification, to a range optimal for the particular biochemical reaction and detection. Generally, the optimal final pH will be in a range of 6.0-9.5, and is dependent on the physical/chemical properties of the polymerases, amplification efficiency and detection.

In the following discussion, a simple hand-held, hand-actuated device is discussed with reference to preferred embodiments. A sample is taken from a donor and the device is operated by a user. In some cases the donor will also be the user.

Biological Fluid Extraction

Samples, including saliva, blood and urine, may be added directly to a device for preparation and conditioning. Alternatively a swab may be used to capture cells. A swab may be a buccal swab, nasopharyngeal swabs, throat swabs, ear swabs, genital swabs, wound swabs, swabs of a contaminated surface, or other swab, used raw or minimally-prepared. The swab material may be an open-celled foam, closed-cell foam, knitted polyester, or flocked fibre. In a preferred embodiment for the application of nucleic acid detection in the host animal, the sample is saliva taken by a swab having a material made from a closed-cell foam attached to the end of a stick acting as a handle. Advantageously a closed cell foam swab material does not capture biological cells and thus this system does not require mechanical or user agitation to release them.

Alternatively, a non-foam material may be used whereby sample is carried on the surface of the swab only. In any case, the material will be compliant such that the effective surface area can initially be large to absorb or adsorb sample and then be compressed to reduce the effective surface area and/or volume such that sample is expelled. The effective area is the amount of surface to which sample can be adsorbed. This is reduced when the shape of the material changes, the volume becomes compressed or the surface becomes folded on itself.

Preferably, the surface or shape of the swab is arranged to maximise the capacity for sample. This may be achieved by adding grooves, undulations, ribs, fins, holes (blind or through) etc. The material should be a biocompatible material, being non-leaching, stable, such as medical grade PP, HDPE, or LDPE.

Figure 2:
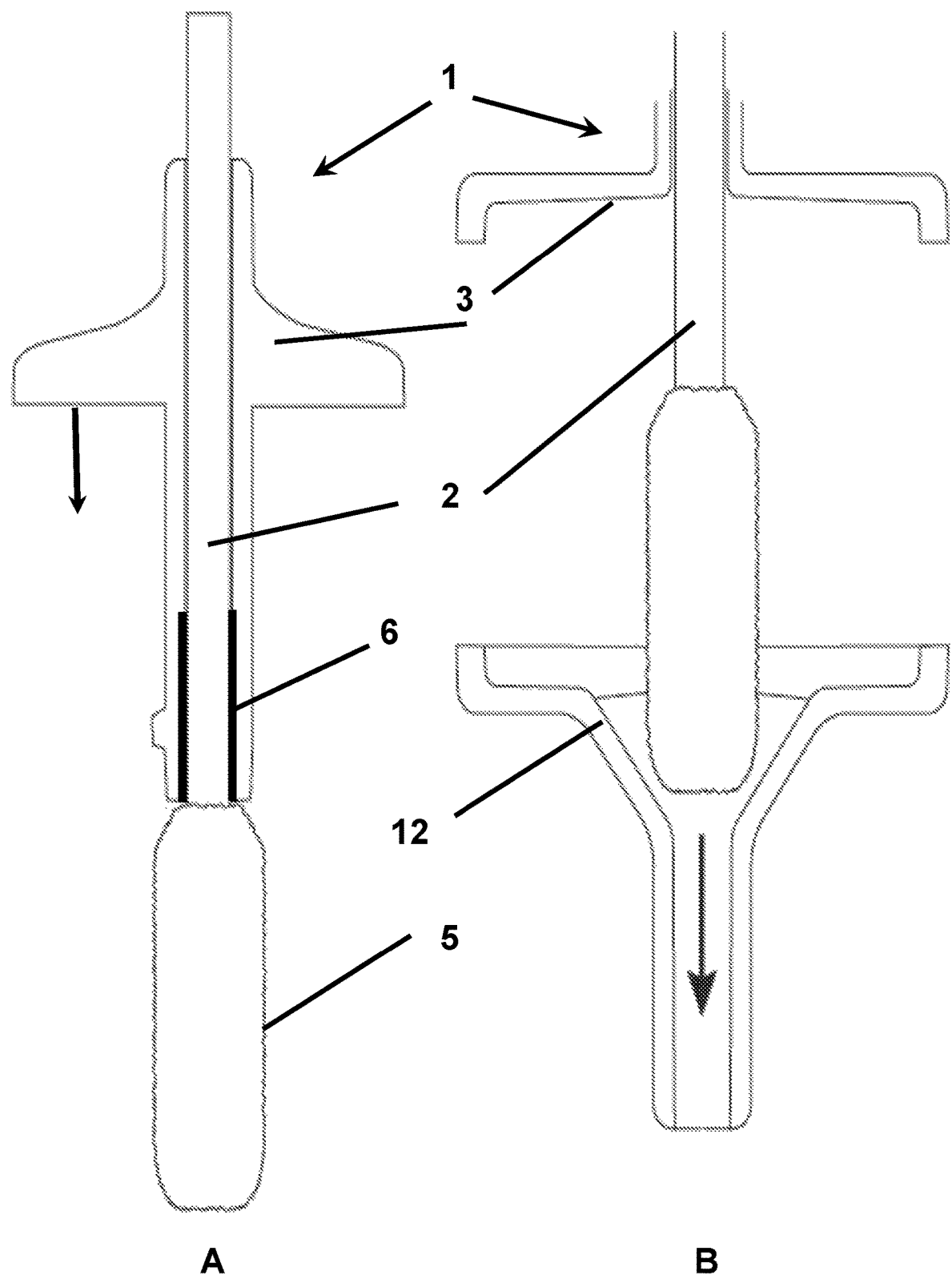
FIG. 2 is a sectioned illustration of a swab (a) with a sliding collar and (b) received by a funnel.

FIG. 2a shows an embodiment of a sample extraction device 1 having a swab 5 for collecting fluid, a handle 2, and a collar 3. The user provides the swab 5 to a tissue to collect a fluid sample and may wipe the swab against the tissue to remove loose cells. Advantageously the surface of the swab may be abrasive to loosen cells from the tissue. These cells adhere to the surface by surface tension of the fluid and are also contained loosely in the folds of the closed-cell foam.

Figure 3:
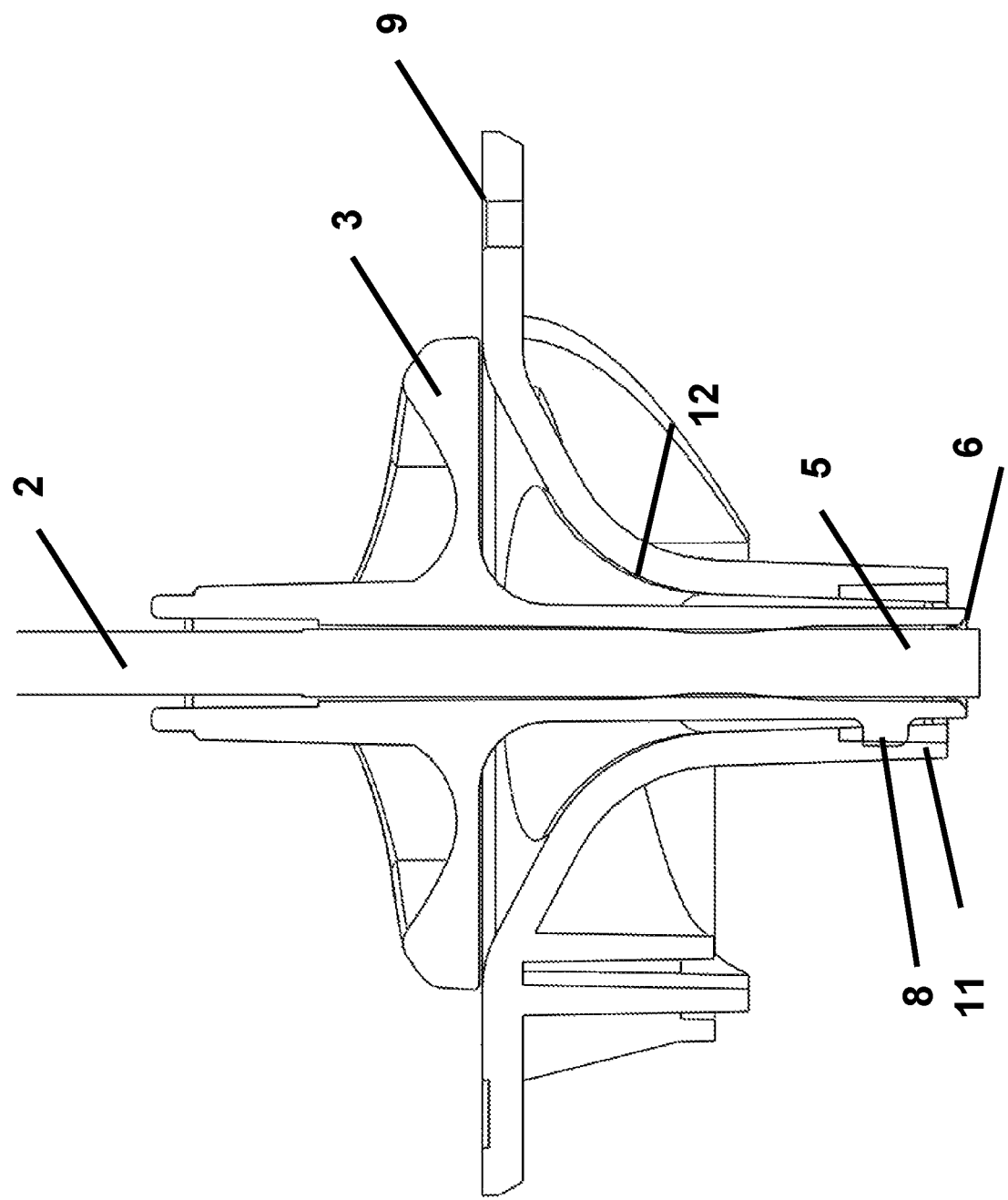
FIG. 3 is a sectioned illustration of a swab in a compressed position.
Figure 4:
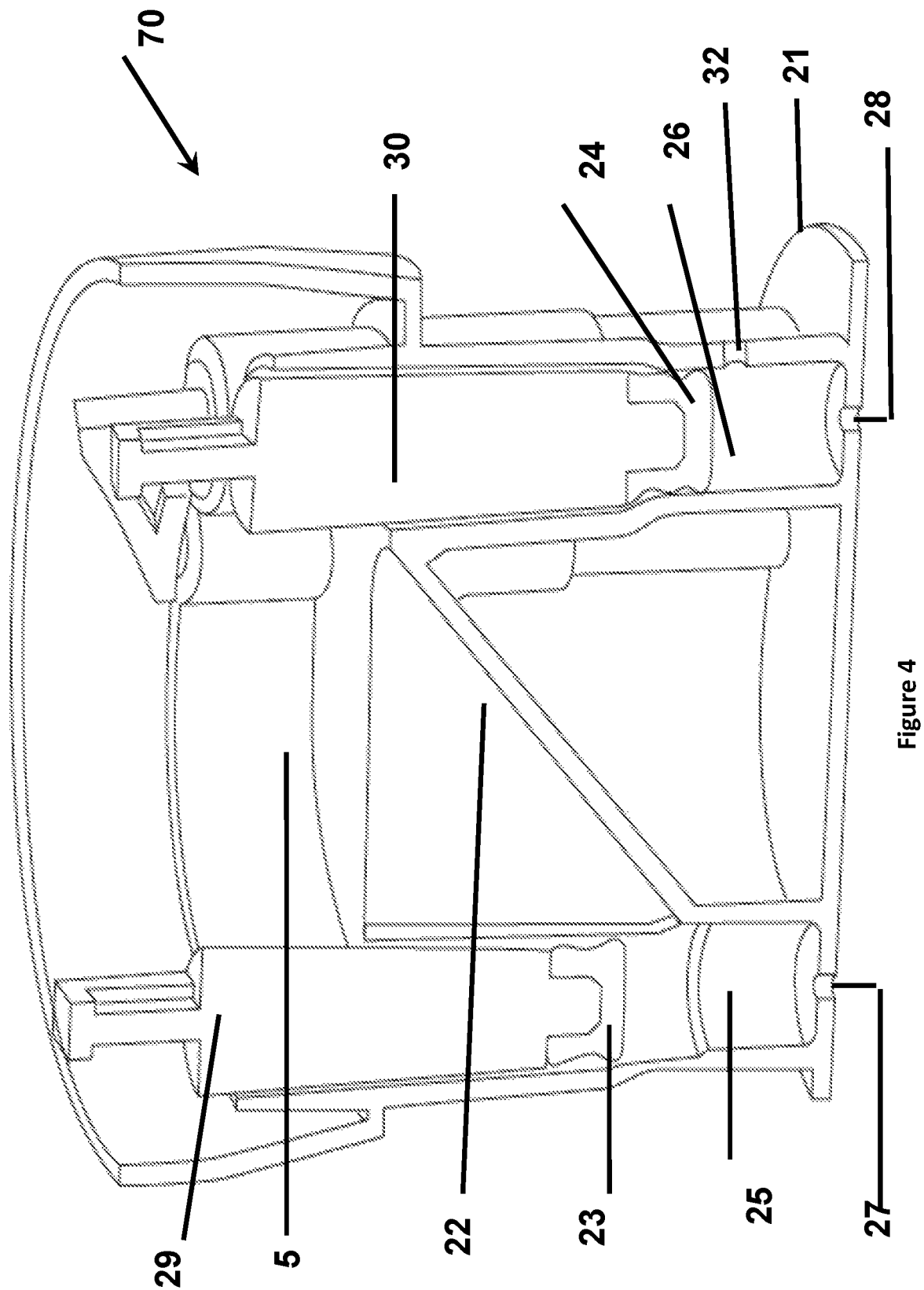
FIG. 4 is a sectioned illustration of fluid dispenser an in initial position.

As seen in FIG. 3 the swab is inserted into a funnel 12 of the sample preparation device 70. Collar 3 then slides relative to the handle to interfere with the swab 5 through a gullet 6. The entry is chamfered to guide the swab into the narrowing gullet. The swab material is thus compressed to release the sample at the location desired. Alternatively the collar may compress the swab 5 in a longitudinal direction (with respect to the handle) against a base in the sample preparation device to release the sample. FIG. 4 shows the collar in the compressing position.

As an alternative to the embodiment of FIG. 2a, FIG. 2b shows a collar 3 fixed on handle 2 to act as a lid. The swab is inserted into the sample preparation device and interferes with a chamber, such as funnel 12, to compress the swab, the exit of the funnel providing the entry port for the sample. The chamber may be a funnel with the cross-section narrowing from the entry being larger than the swab to a cross-sectional dimension that maximises the compression of the swab (e.g. substantially equal to the cross-section of the swab cross-section when compressed or swab when compressed plus handle). The chamber may have a cross-section substantially similar to the swab when uncompressed and have a base to act upon the swab to compress it longitudinally when the extraction device is inserted. When the swab is fully inserted, the lid 3 prevents contaminants entering or fluid leaving the device 70.

In either embodiment, the extraction device 1 and sample preparation device 70 are locked into this compressing position by a detent comprising a protruding portion 8 and void 11 (either of the extraction device (on collar or handle) or sample preparation device may have the protruding portion or void). Thus the fluid cannot be accessed by the user once engaged and therefore cannot be deactivated without the use of excessive force. This is advantageous for diagnostic testing to separate the sample from the user environment. The action of inserting the swab into the sample preparation device accomplishes both compression of the swab and locking into this position.

The volume of the swab and its compression ratio determine the amount of fluid transferred from the material to the sample preparation device. Preferably the sample volume released by the swab is greater than 50 ul, greater than 100 ul, greater than 200 ul, or greater than 400 ul. Preferably the sample volume captured by the swab is less than 2000 ul, less than 1500 ul, or less than 1000 ul.

Squeezing the swab fills an open cylinder in the sample preparation device, with any excess fluid flowing over the top of the open cylinder. As seen in FIG. 4, the fluid travels from the swab 5 along a channel 22 having an incline to fill the cylinder 25. The angle of the incline should be greater than 25° from the horizontal, preferable greater than 45° to encourage flow and avoid any influences of the device being held slightly off vertical.

Donor Preparation

Saliva fluid collected from a donor can contain substance(s) that interfere with subsequent genetic and/or protein diagnostic assays (e.g. nucleic acid amplification reaction, DNA sequencing). For example, in a nucleic acid amplification reaction, the interfering substance(s) can inhibit nucleic acid amplification, decrease amplification efficiency and/or increase non-specific amplification. As an additional measure to minimize or in some instances eliminate the undesirable substance(s) in the saliva fluid, a mouthwash rinsing procedure can be performed prior to the collection of the saliva. The mouthwash rinsing procedure can be performed immediately after brushing, eating, drinking etc. without additional waiting period before the collection of saliva sample. In the mouthwash rinsing procedure, an individual rinses their mouth with a mouthwash for a specified amount of time, preferably between ten seconds to two minutes, more preferably between twenty to fifty seconds, before emitting the mouthwash from the mouth. The mouth is next rinsed with water at least twice, preferably at least five times, to remove or reduce residual mouthwash in the saliva prior to the collection of saliva fluid. The saliva fluid can be collected by a swab.

The following is an example of mouthwash rinsing protocol:
1) Rinse mouth with 10-30 ml of Listerine Zero™ (e.g. a half to full Listerine bottle cap) for 20-30 seconds;
2) Emit the mouthwash from the mouth;
3) Rinse mouth with 10-30 ml of water;
4) Repeat step 3 for additional five times;
5) Wait 1 to 2 minutes before saliva collection;
6) Collect saliva by spitting the saliva into a collection vessel.

A mouthwash is typically a solution that has antiseptic and/or antimicrobial properties. The mouthwash may be home-brewed, or from an organic or commercial source. However, a solution consisting of just salt and water is not desirable.

The mouthwash may contain alcohol. It is preferable that where mouthwash containing alcohol is used, there is provided additional rinsing steps with water to remove or minimize the amount of residual alcohol in the saliva prior to saliva collection. This is because the residual alcohol in the saliva sample may interfere with subsequent diagnostic assays. Preferably the mouthwash does not contain alcohol.

Mouthwash from a commercial source may be: Colgate Plax™ (alcohol or alcohol free), Listerine™ (alcohol or alcohol free), Corsodyl™, Dentyl pH™, Oral-B™, Scope™, Astring-O-Sol™, Cepacol™, Sarkan™, Tantum verde™ and Organic pharmacy™.

In an embodiment, the system, preferably the sample preparation device comprises a container of mouthwash.

Sample Preparation Device

The sample preparation device 70 comprises a housing within which are several fluid dispensers and receptacles for containing and/or mixing fluids. The dispensers and/or receptacles may be provided by cylinders 25, 50, 46, 52, 26 and plungers 29, 33, 30, 35, 36. FIG. 4 show the dispensers in the initial position. The plungers move downwards to reach a final, dispensed position. Plunger 29, connected to bung 23, strokes within cylinder 25 to dispense the fluid through exit port 27. Plunger 30, connected to bung 24, strokes within cylinder 26 to dispense the fluid through exit port 28.

Sets of plungers are arranged to move concurrently to dispense separate fluids into a receptacle to mix these fluids. Subsequently another set of plungers may move concurrently to dispense the mixed fluid and another fluid into yet another receptacle to mix those fluids. This combination of subsequent and concurrent dispensing may be repeated to allow additional mixing steps in a sample preparation process. There is a microfluidic channel 62 communicating between two or more dispensers and the receptacle, the channel preferably providing a tortuous path to increase mixing. The channel may follow a serpentine path, have channel restrictions, and/or have a roughened surface to create turbulence in the fluid and increase the effective length compared to the distance between ports. The channel cross-section may be relatively small to increase fluid velocity and boundary effects, thereby encouraging mixing. Preferably the cross-section is less than 1 mm$^2$, less than 500 um$^2$, or less than 200 um$^2$.

Figure 9:
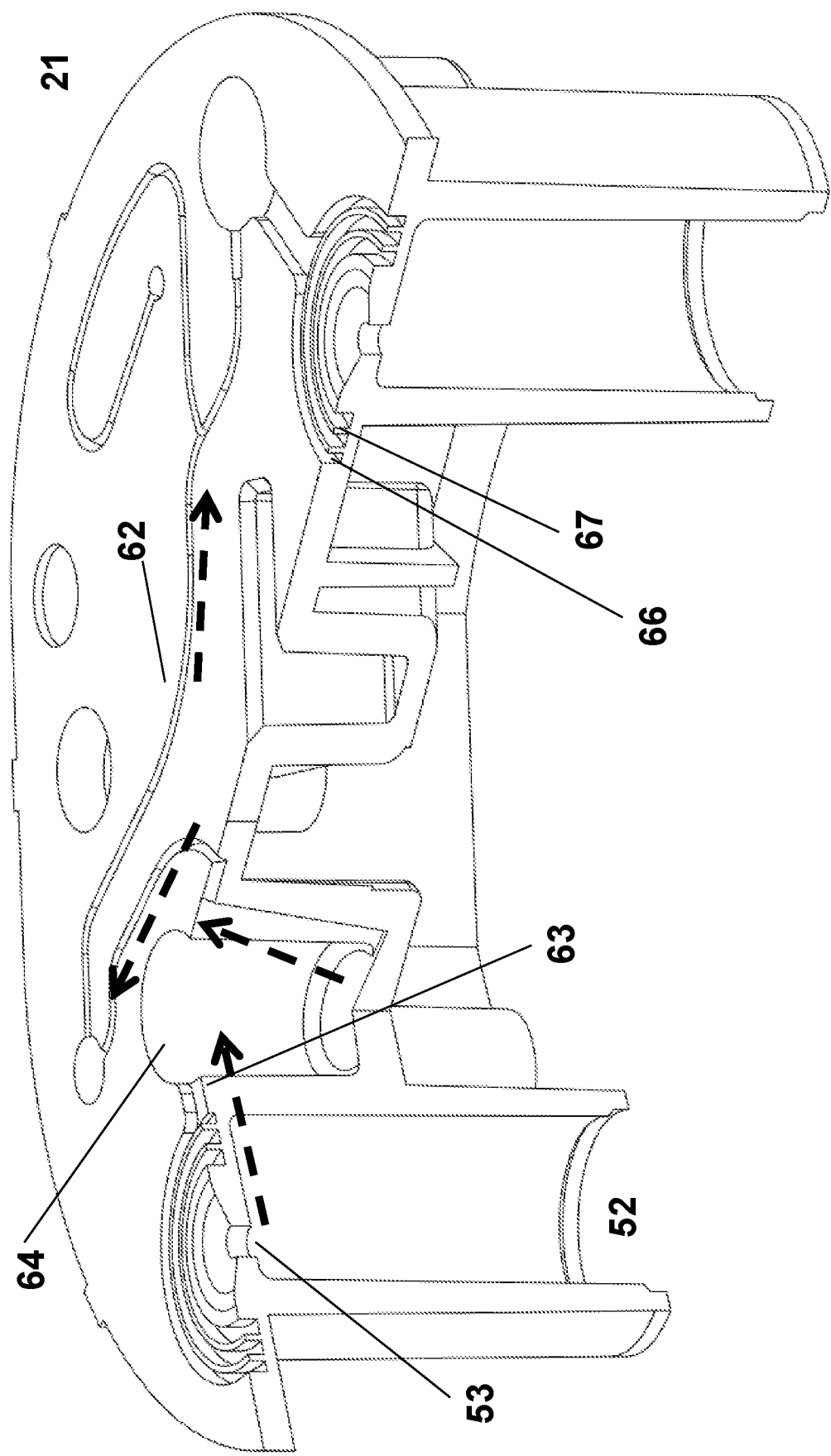
FIG. 9 is a sectioned illustration of a base with fluid channels.
Figure 10:
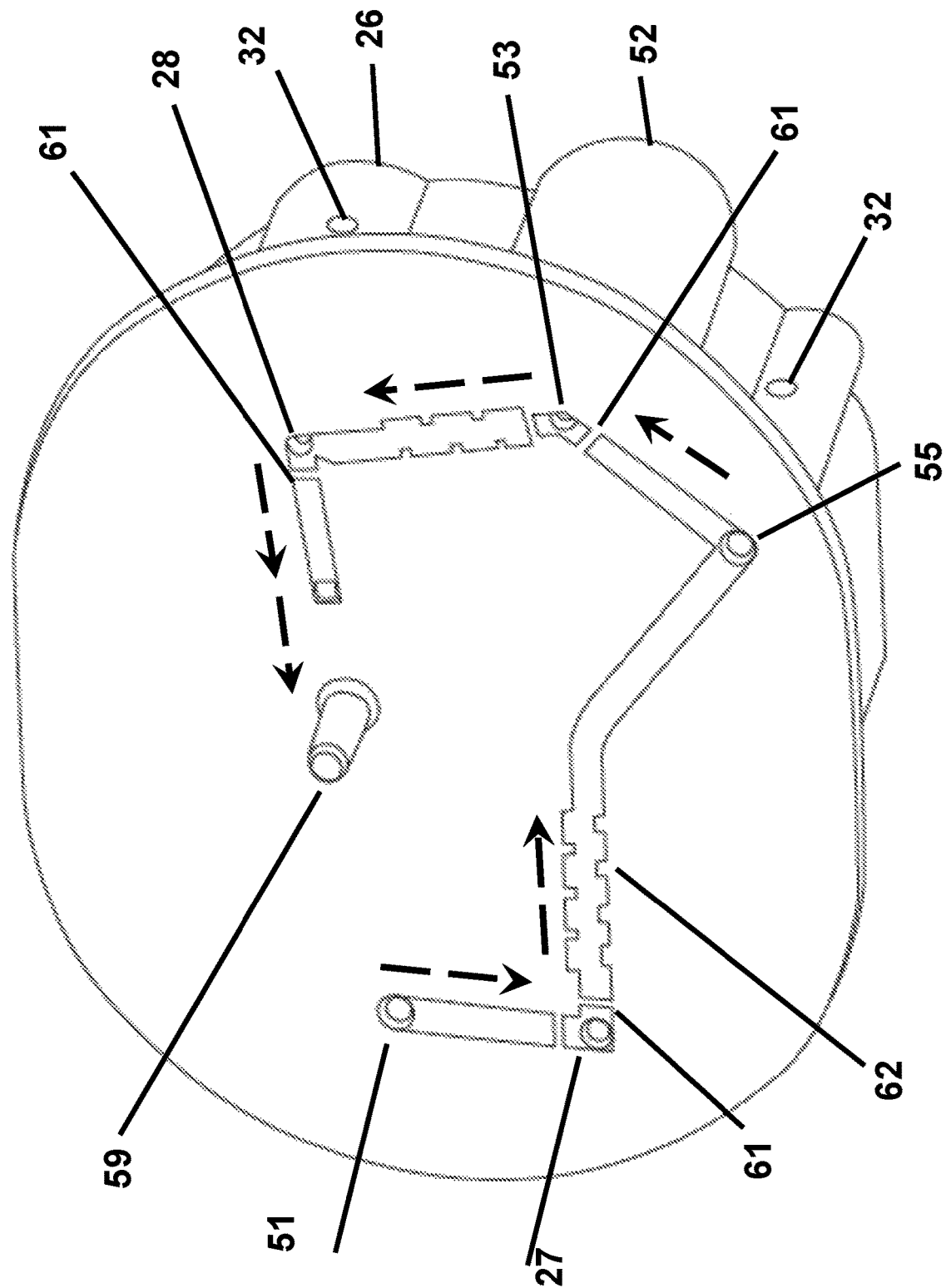
FIG. 10 is an illustration of an alternative base with fluid channels.

FIGS. 9 and 10 are alternative embodiments showing the underside of base 21 having channels 62 formed therein. Arrows indicate the direction of fluid flow. The channels enable the fluid exiting ports 51 and 27 to flow and mix before entering port 55. Similarly ports 55 and 53 flow into port 28.

The device allows a plurality of initially separate fluids to intermix and flow together along the channel 62. The stroke of each plunger and the cross section of the cylinder precisely determine the volume of fluid dispensed. A cylinder may have a bleedhole to allow air or fluid to exit therethough in preference to the cylinder end, in which case the volume depends on the stroke of the plunger after the bleedhole position.

Actuation of the plungers may be made in a variety of ways. Automated means may be employed to actuate the dispensers using hydraulics, yokes, switches, solenoids and/or motors in order to covert comfortable user action into controlled and effective motion. However to reduce costs and avoid the need for a powered instrument, preferably the device is actuated by a user using simple mechanical means such as a cam-follower.

Figure 6:
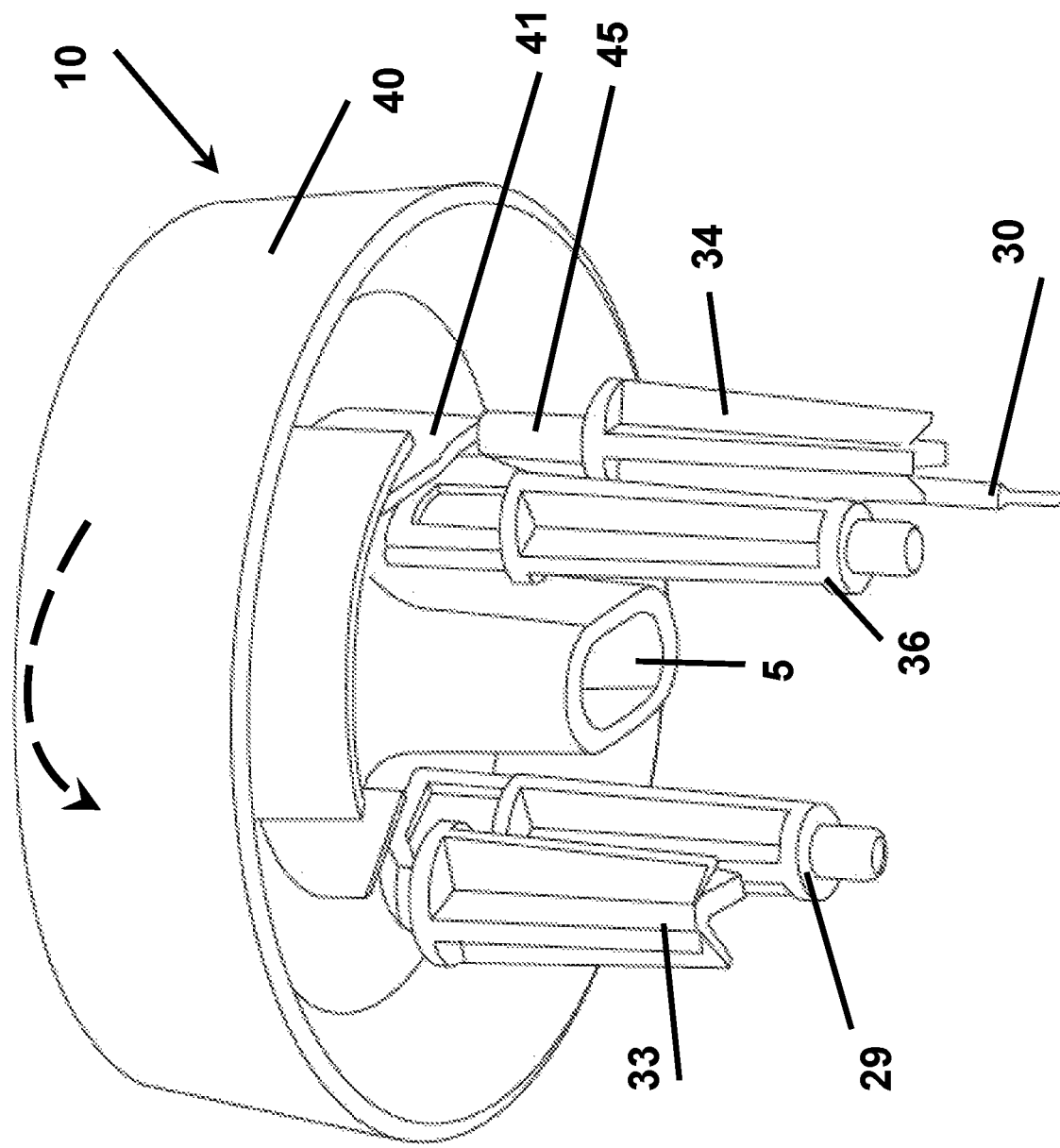
FIG. 6 is an illustration of plungers and cams.

A cam is a mechanical device having a shape or profile that engages a follower to provide a predefined output motion on the follower. Thus constant motion of the cam can produce a varying, almost arbitrary, desired motion on the follower. In one embodiment of a cam shown in FIG. 7, semi-circular tracks 41, each located at a fixed radius from the rotational centre, provide a cam surface whose distance from a surface 9 defines the displacement of a follower. As seen in FIG. 6, the follower 45 rides on the surface of this cam track 41 and is constrained to move in a direction orthogonal to the plane of surface 9.

In a preferred embodiment, the user twists a rotatable cap 10 connected to surface 9 which displaces sets of plungers along concentric circular cam tracks 41. The cam tracks translate the rotating motion of the cap 10 into sequential and simultaneous motion for the plungers. Rotational hand actuation and the gearing provided by the cams advantageously provides smooth and continuous rate of motion compared to linear hand motion such as a push or pull.

Figure 7:
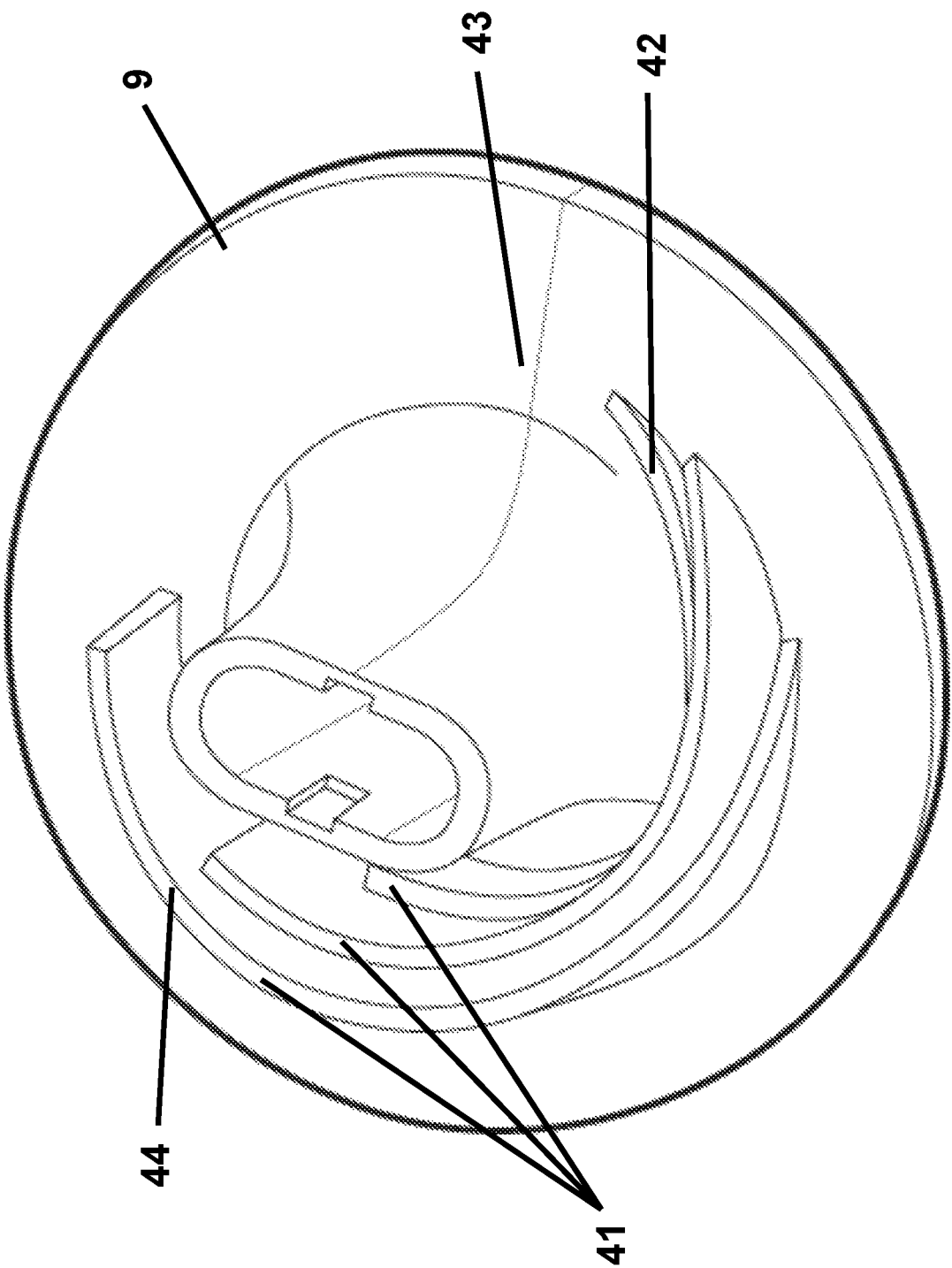
FIG. 7 is an illustration of a set of cam tracks.

As seen on FIG. 7, inclined portions 42 translate the rotational motion into vertical motion. Flat portions 43, 44 provide dwell periods during which rotation of the cap does not translate into vertical motion. The motion of the plungers is designed to be non-reversible or unidirectional meaning that reversing the user motion does not result in retraction of the fluid dispensed. The cam does not positively engage the follower so that the cam can only push the follower and not pull it. A single cam track may have three sequential portions (i) a first dwell portion 43 before the plunger moves (ii) an incline portion 42 during which the plunger moves and a (iii) a second dwell portion 44 during which the plunger is locked down in the cylinder. The incline portion transitions between the first and second dwell position. Thus once actuated, the plungers are kept in the dispensed position, preventing flow-back of fluids from subsequent plunger actuations. Additionally this prevents reuse of the device, which may be important from a health and quarantine perspective.

To prevent reverse rotation of the cap 10 and provide audible feedback to the user, a ratchet may be employed between the cap 10 and housing. The ratchet action may be continuous throughout the rotation or provided at key steps in the process. A ratchet may be provided by a void on one of the cap and housing cooperating with a protrusion on the other of the cap and housing. The geometry of the void and protrusion surfaces are arranged to slide past each other in one direction but lock in the other direction.

Figure 8:
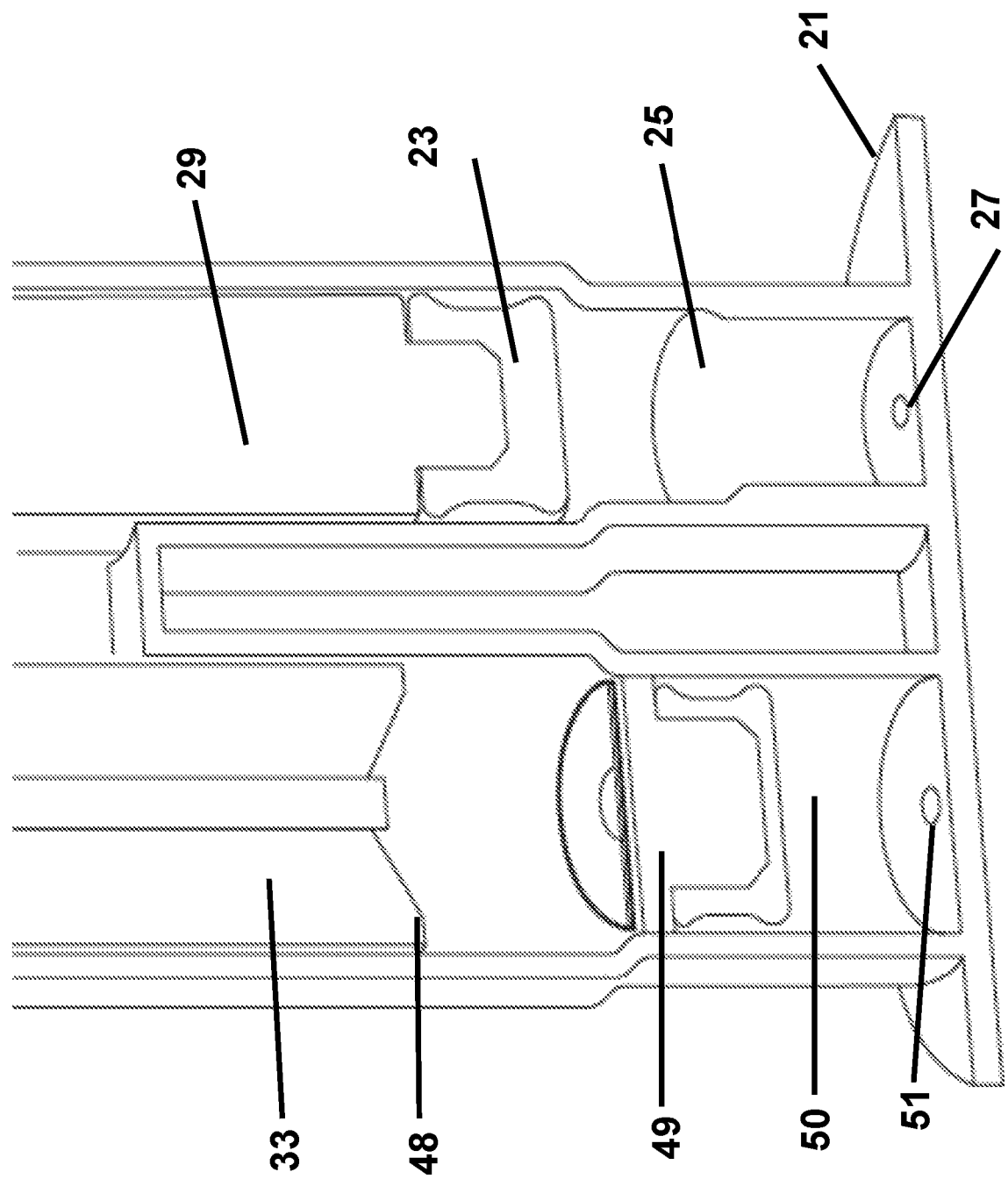
FIG. 8 is a sectioned illustration of a plunger and plunger tip in chambers.

A first type of dispenser, exemplified in FIG. 8, may comprise a first type of cylinder 50, a bung 49, pierceable seal across the cylinder, and a plunger 33 having a cutter 48. The cylinder with seal provides a sealed vessel for the storage of a fluid. The plunger acts on the bung to displace the fluid. FIG. 8 shows the initial position of the dispenser wherein the bung is located within the cylinder, separated from the plunger by the seal.

The pierceable seal provides a barrier in order to preserve the fluids contained within during shipment or storage and to prevent transmission or evaporation losses before actuation and thus ensure appropriate mix ratios.

The first type of cylinder is prefilled with a fluid (e.g. lysing buffer, reagents for nucleic acid reactions). The cylinder is sealed on both ends to prevent contamination, degradation and fluid escape. On a first end, the cylinder is sealed with a membrane, such as a foil, which is pierceable by a cutter 48 on the end of the plunger engaging that cylinder's first end. On a second end, the cylinder is attached to a base 21 having a fluid exit port. The exit port is initially sealed by a membrane covering the bottom of the base. This membrane is preferably attached to the base by an adhesive. The membrane may be a heat-sealed foil or gasket or pressure sensitive adhesive.

During use, the plunger is moved towards the cylinder first end, pierces the membrane, and displaces the fluid by a predetermined amount. The pressure in the fluid breaks the seal on the cylinder second end such that the fluid is free to move through the channel.

The bung and plunger play the role of a plunger or piston but their separate manufacture enables the provision of an end that is soft enough to seal against the cylinder walls whilst hard enough to be pushed and pierce the membrane. The bung may have sealing edges 47 to deformably contact the wall of the cylinder. A plunger having an integrated bung may be created using a two-part injection process, where two materials are added separately to provide the two functions of strength and sealing.

In one embodiment, the base 21 of the sample preparation device is used to define a set of microfluidic channels, microfluidic ports and microfluidic chambers. The channels and chambers are defined during injection moulding or machined into the base leaving one side of the channels and chambers open. A flexible membrane is fixed to the base to cover the open side of the chamber and channels and cover the ports to isolate the reagents in the dispensers from the environment.

Walls (66, 61) act as a dam between the dispenser port and the channel and prevent exposure of the reagents in the dispensers (such as lysis or enzymes) to the environment. Under hydraulic pressure at the port, the membrane flexes at a point on a surface of the wall contacting the membrane to permit fluid to exit the ports.

In one embodiment, shown in FIG. 9, a volume/void 66 substantially surrounds the walls 67 which surround the port 53 such that, regardless of the point of flexure near the port, the fluid will continue to a channel rather than leak across the base surface contaminating other areas. The void may be a part of the channel. Preferably the walls and void are annular. There may be one or more sets of walls and voids concentrically surrounding a port with least one wall contacting the membrane. The walls and voids are arranged such that the fluid preferentially substantially fills a void before flowing over a wall to the next void. Preferably the walls are formed integrally within the base 21. As an alternative, the walls may be flexible, bending or frangibly disintegrating under the fluid pressure. For example, a silicon wall may be deposited around the port.

In another embodiment, shown in FIG. 10, the port is only separated from the channels 62 by a dam 61 at a single point, which may be located within the channel 62. The flexible membrane flexes above the dam to permit fluid to flow over the dam and continue along the channel.

The user action of pressurizing the fluid can lead to great uncertainty in the timing of the fluid. For example, variations in the cam-follower parts, user force, and membrane adhesion to the base mean that the point of flexure can vary, which in turn varies the point at which the fluid is delivered to a location or mixes with a second fluid being dispensed. The membrane may move early with low fluid velocity or move late with high velocity. Also, high velocity is more likely to entrain air bubbles in the flow.

Thus in additional to walls 67 and void 66, the port 53 may be separated from the channel 62 by connecting channel 63, reservoir 64 and exit slot 65. These microfluidic components have the effect of removing variation in timing and velocity of the fluid leaving the port 53 to provide a smooth, precisely timed flow entering channel 62. A reservoir may be a sufficiently large void 66 or a separate chamber 64, as shown in FIG. 9. The volumes of the microfluidic components (such as reservoir, void and channels) are chosen to time the exit of the fluid to mix with another fluid in the channel 62.

By allowing the bursting fluid to flow into a reservoir 64, which can fill early and slowly, or late and quickly, either way completely filling the reservoir, ensures that exit from the reservoir occurs at a more predictable time than the initial burst itself. The flow of the fluid is determined by surface tension rather than gravity or positioning. The reservoir and reservoir exit are configured so as to ensure that the fluid completely fills the reservoir and the air leaves the reservoir before the fluid exits. The dimensions of the exit are smaller than those of the reservoir. Thus the fluid wets the entire reservoir before exiting. Preferably the area of the exit port is less than 20% of the reservoir surface area, more preferably less than 10%. Preferably, in cross-section, the width or diameter of the exit port is less than 20% of the reservoir perimeter, more preferably less than 10%. The skilled person will appreciate how the relative dimensions can be designed based on fluid properties.

A second type of dispenser is initially empty. As seen in FIG. 4 (right side) this dispenser may comprise a second type of cylinder 26 having a plunger 30 engaged at a first end and a second end attached to a base having a fluid port 28. Two or more fluids, having mixed in a first channel connected to the fluid port, enter the second type of cylinder to fill a portion of it. Excess fluid and air may exit through a bleedhole 32 located in the side wall of the cylinder. When the plunger is stroked in the cylinder, it first displaces the remaining air out through the bleedhole and then displaces the fluid back out through the fluid port in the second end of the cylinder. Alternatively, the plunger may stop before the end of the cylinder such that air contained within the cylinder does not get pushed in the channel. The fluid moves along a microfluidic channel different from the first channel that brought the fluid into the cylinder. The fluid cannot move back through the first channel because the (incompressible) fluid is blocked at one end by the plunger in the previous cylinder, which itself is locked in position by the flat portion 44 of the cam track.

The mixed fluid in the second channel may enter another receptacle to mix with another fluid or flow to a sensor to be detected.

A third type of dispenser is provided to receive the biological sample either from the swab as described above, or from a syringe or using a shaped collection vial built into the sample preparation device. As exemplified in FIG. 4, the dispenser may comprise a third type of cylinder 25 having an opening at a first end to receive a plunger and an exit port 27 at a second end fixed to a base 21. The sample is gravity fed along inclined channel 22 to enter the cylinder via the first opening or via a port in the wall of the cylinder 25. A first user actuation engages plunger 29 into the cylinder 25. A bleed hole or missing portion of the wall of the first cylinder allows fluid to escape until a predetermined start position. Further stroke of the plunger from the start position to the end position defines a known volume to exit the cylinder.

The plunger 29 may be initially removed from the cylinder 25 and upon actuation moves to engage cylinder 25. The top of the cylinder 25 may be tapered such that the plunger has some lateral tolerance before engaging and sealing against the sides of the cylinder.

In a preferred embodiment, a fluid from the third type of dispenser mixes with fluid from a first type of dispenser to enter the second type of dispenser.

Figure 5:
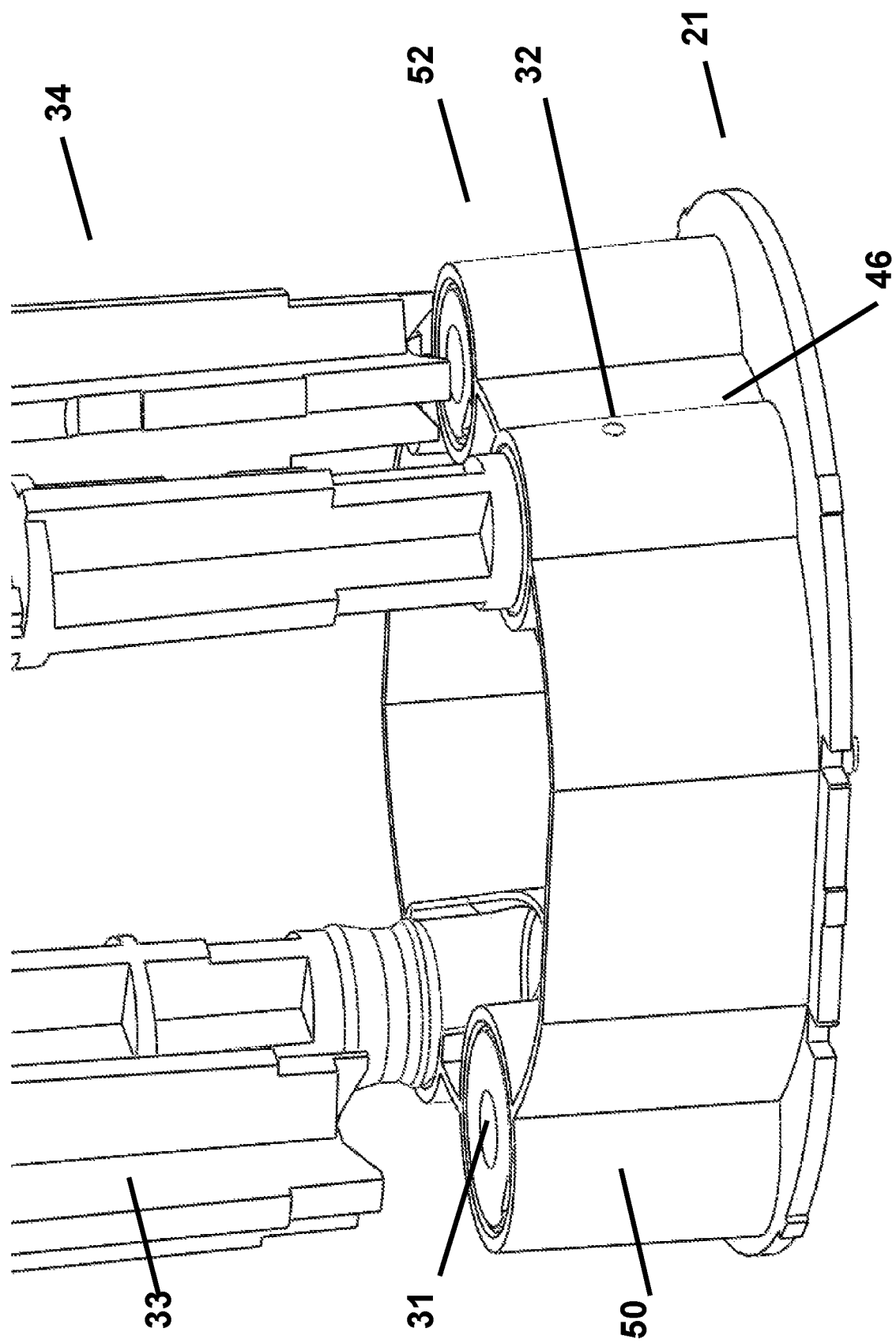
FIG. 5 is an illustration of a plurality of plungers and cylinders.

In a preferred embodiment shown in FIGS. 5 and 9, there are 5 cylinders/plungers: a first cylinder/plunger for receiving the sample fluid; a second cylinder/plunger for containing a lysing buffer; a third cylinder/plunger for receiving and mixing the lysing buffer and sample; a fourth cylinder/plunger for containing reagents for a nucleic acid reaction; and a fifth cylinder/plunger for receiving and mixing the lysing buffer/sample mixture with the reagents for a nucleic acid reaction. The second and third cylinders as shown are examples of the first type of cylinder. The third and fifth cylinders as shown are examples of the second type of cylinder. FIG. 9 shows a twisting action on cap 10, which rotates the cam tracks and displaces the plungers. Preferably the cap has surface texture features 40 to improve grip such as a knurled surface or indents.

In one embodiment, pairs of plungers are arranged to move together, to enable simultaneous expulsion of fluids from cylinders and therefore allow mixing during flow.

Preferably the pairs are formed together, more preferably as an integrated injection moulded part.

Sensor Cartridge

Once the fluid sample has been prepared, it is transported to the sensor cartridge 80, which has sensor chip 100 located within a housing. The final mixed fluid flows along a channel and enters the sensor cartridge housing via nozzle 59 (see FIG. 9).

Figure 13:
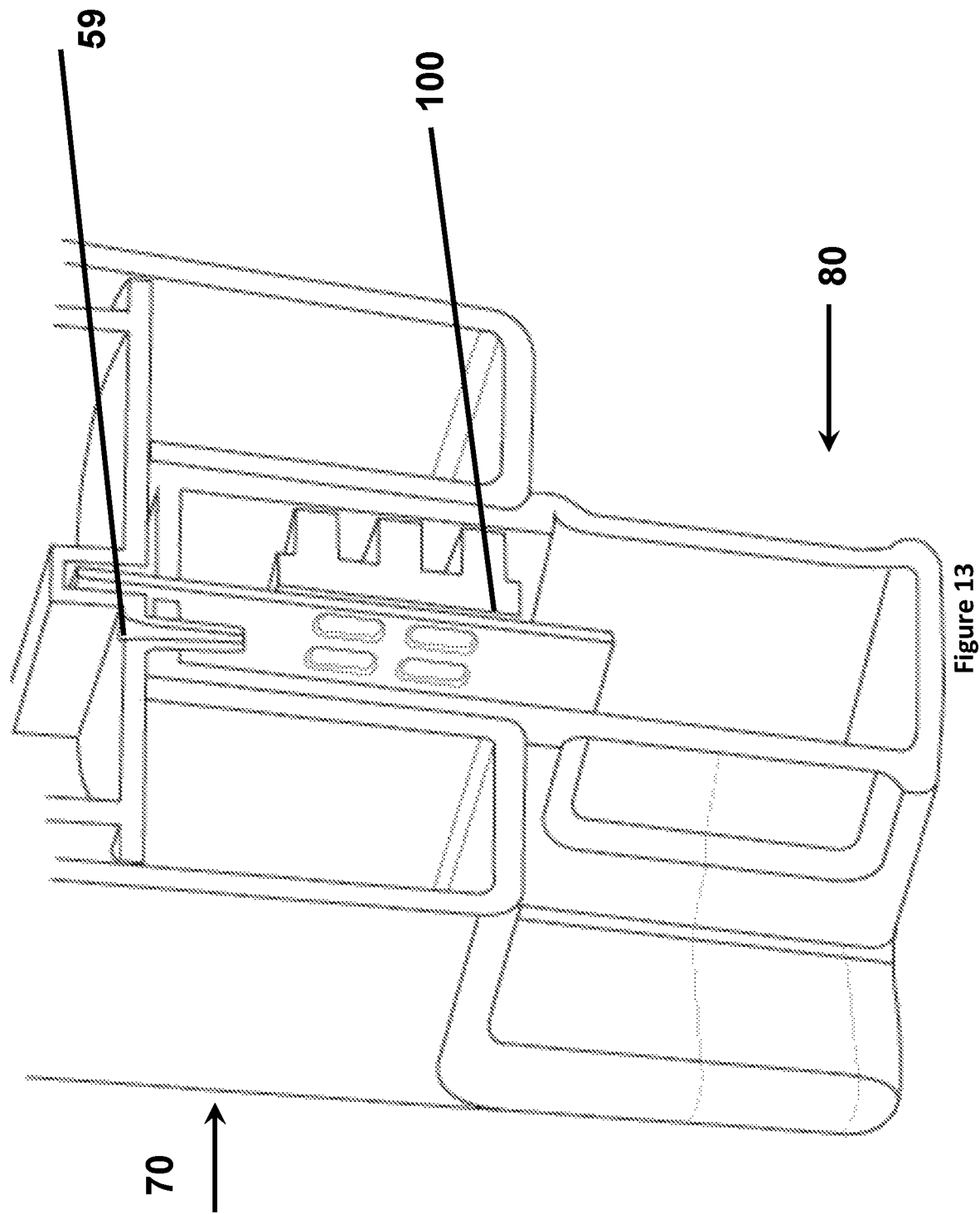
FIG. 13 is a sectioned illustration of a sample preparation device with a cartridge engaged.
Figure 14:
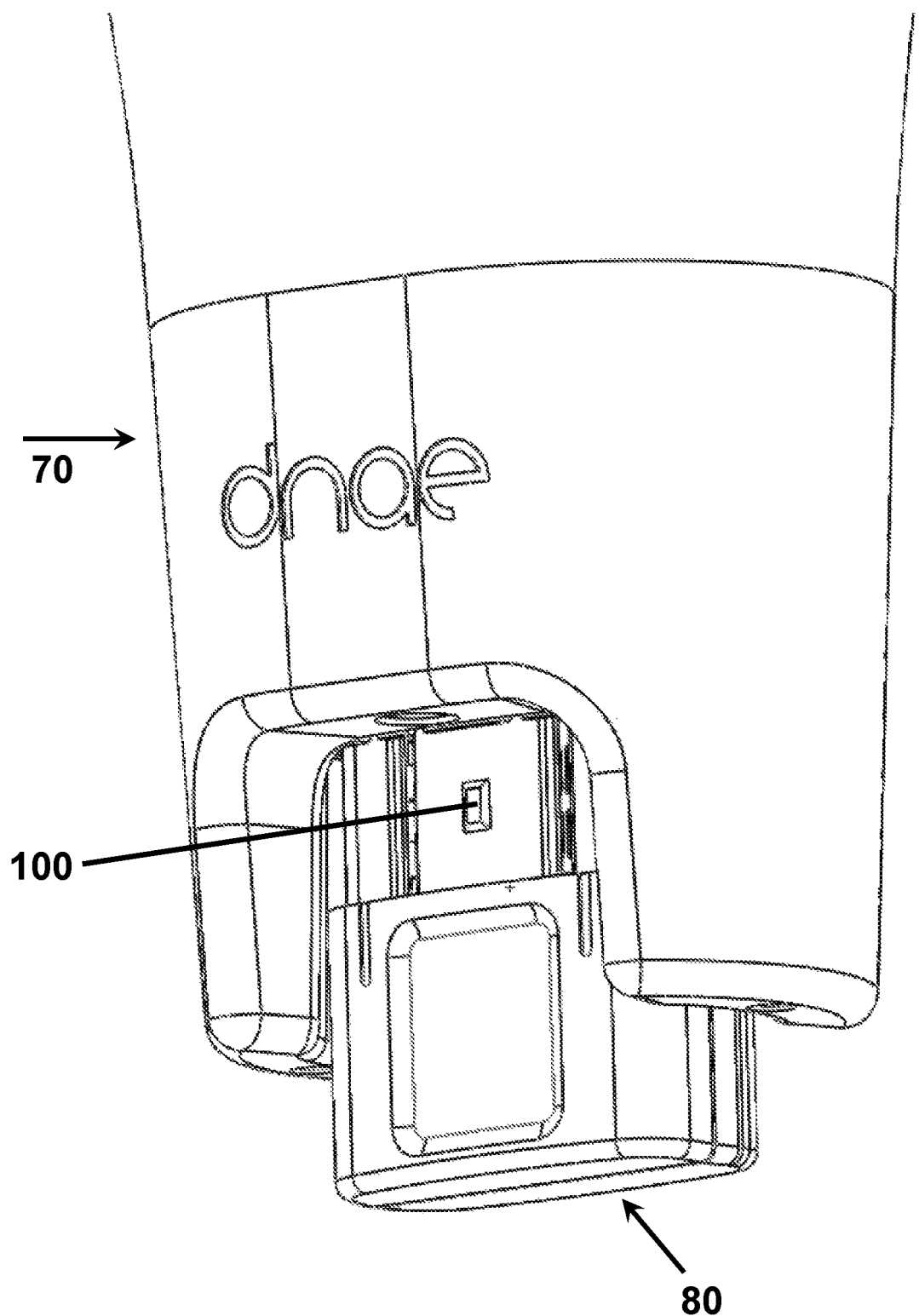
FIG. 14 is an illustration of a sample preparation device with a cartridge partially engaged.

The cartridge may be disposable, in which case: there need only be sufficient reagents for one reaction; the interior need not be user accessible or serviceable; and the system need not have peripheral devices to clean or refurbish the cartridges. In preferred embodiments, the sensor cartridge housing is initially located at least partially within or abutting the sample preparation device. In FIG. 13 the sample preparation device is shown with the sensor cartridge engaged. In FIG. 14 the sensor cartridge is shown party removed.

Figure 15:
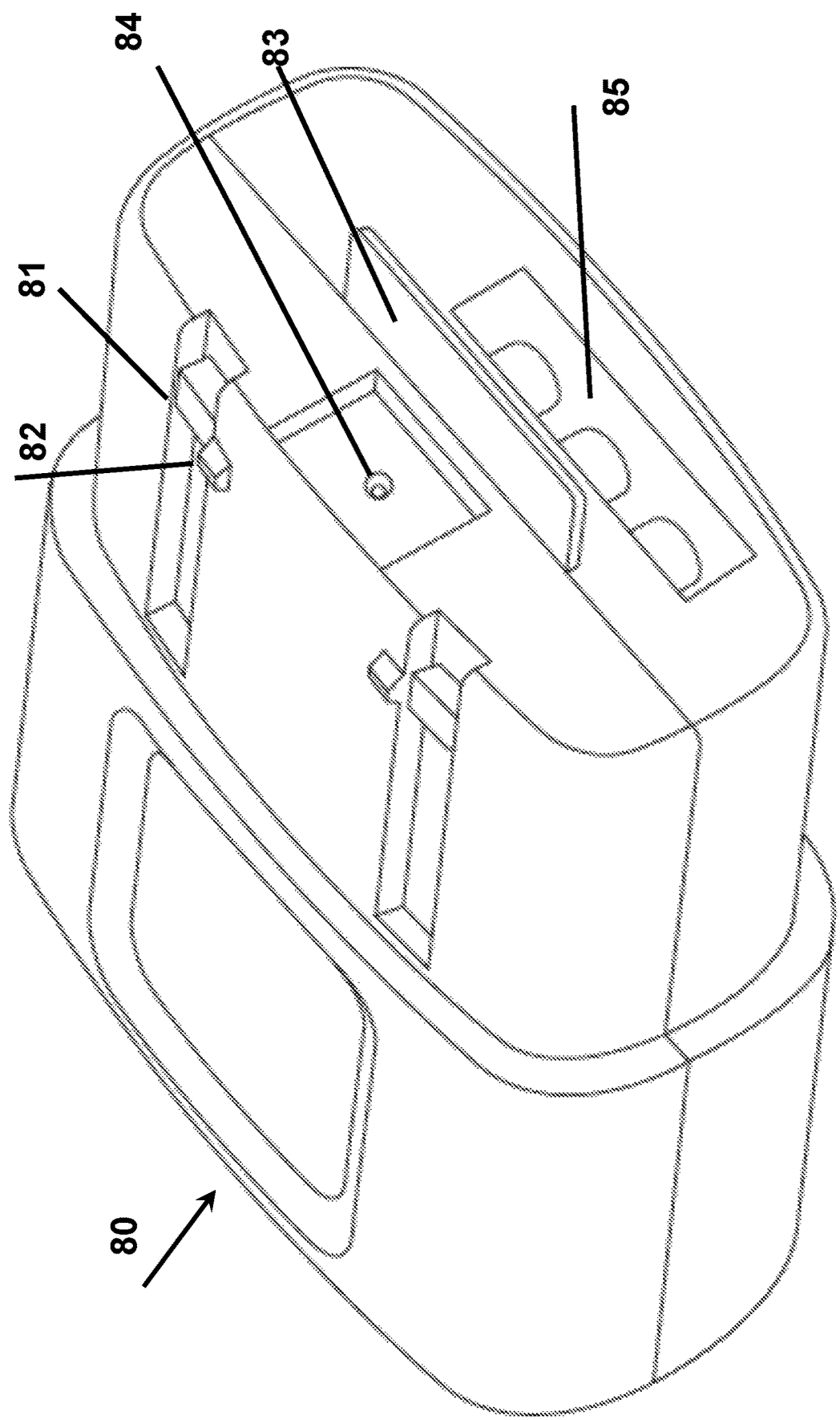
FIG. 15 is an illustration of a cartridge.

The sensor cartridge is shown in sectioned FIG. 15 having a fluid sample port 84, air port 85, electrical connector 83, sealing block 87, microfluidic containers 101, heat sink 105, and sealing wedge 86, all within the housing. The port 84 is defined by a hole through one or more layers, which layers provide an absorbing or sealing function. Preferably, to prevent spillage of fluid during transfer, one layer is a gasket arranged to seal around the nozzle 59 and another layer is an absorbent material.

Once inside the sensor cartridge, the fluid flows across the sensor chip. A plurality of microfluidic containers 101 are provided to receive the fluid, each exposed to one or more sensors. The top of the container may be initially open for the fluid to flow into, becoming sealed before monitoring by the sensor. To ensure even and sufficient distribution of the fluid, there is a surface above the sensor surface to create a gap for fluid flow. The gap height is designed to provide wicking action along the surface of the chip. The gap should be designed such that the fluid wicking force should be greater than the gravitational force. The gap may be substantially constant or be reduced towards the end distal from the entry port (to provide continuous wicking action as the fluid is taken up into the wells. The optimal height will depend on a variety of factors such as materials used, fluid viscosity and fluid volume. In preferred embodiments the gap height is greater than 100 um, greater than 300 um, or greater than 700 um and less than 3 mm, less than 2 mm, or less than 1 mm. In preferred embodiments, surfactants such as Triton, Siloxane, BSA, CHAPS etc. coat the wells and/or chip surface to improve flow.

A microfluidic volume or microfluidic container refers to a structure of micrometer dimensions designed to receive and retain a fluid. For example, microfluidic volumes may be a channel, chamber or well.

Figure 16:
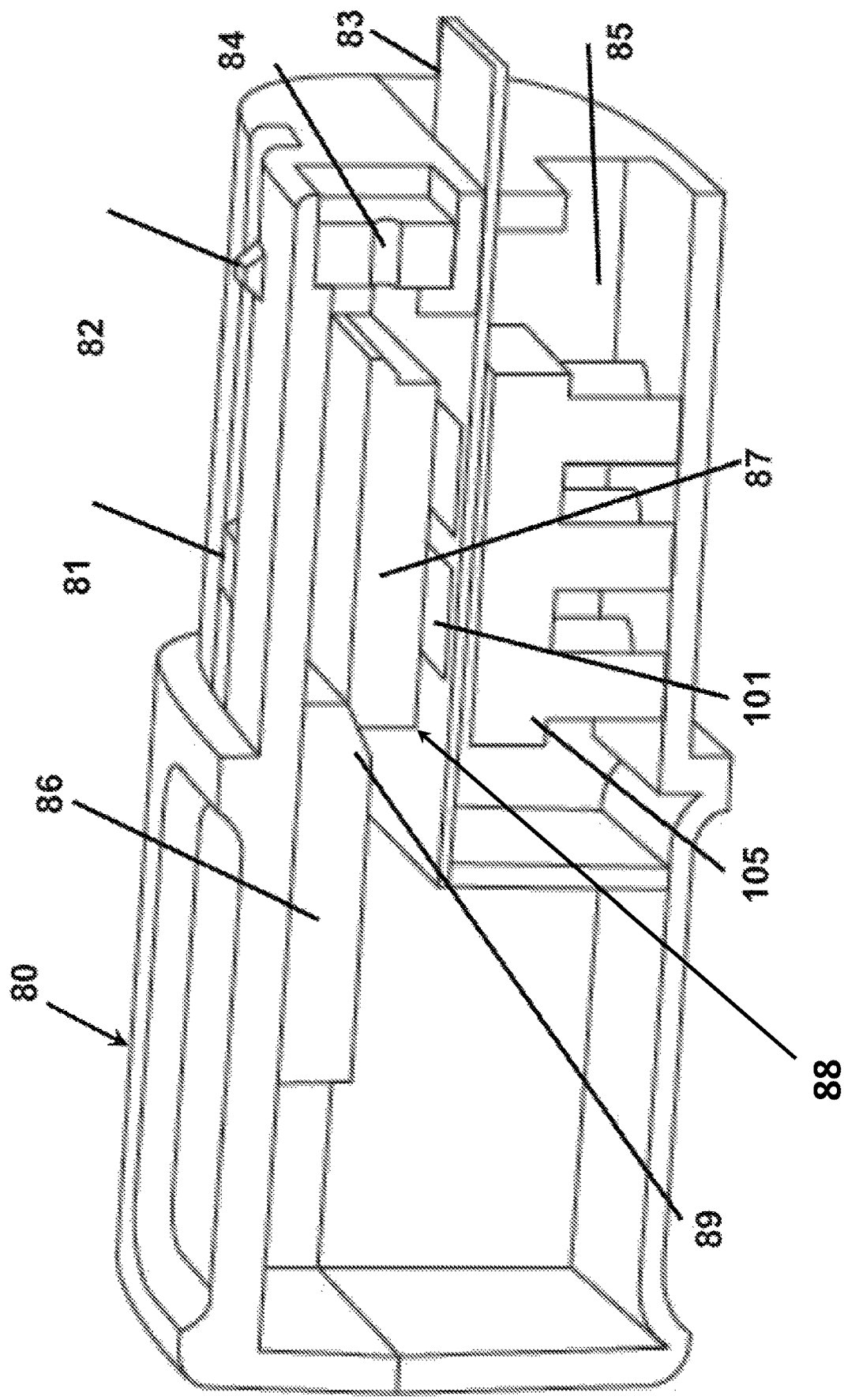
FIG. 16 is a sectioned illustration of a cartridge before actuation.
Figure 17:
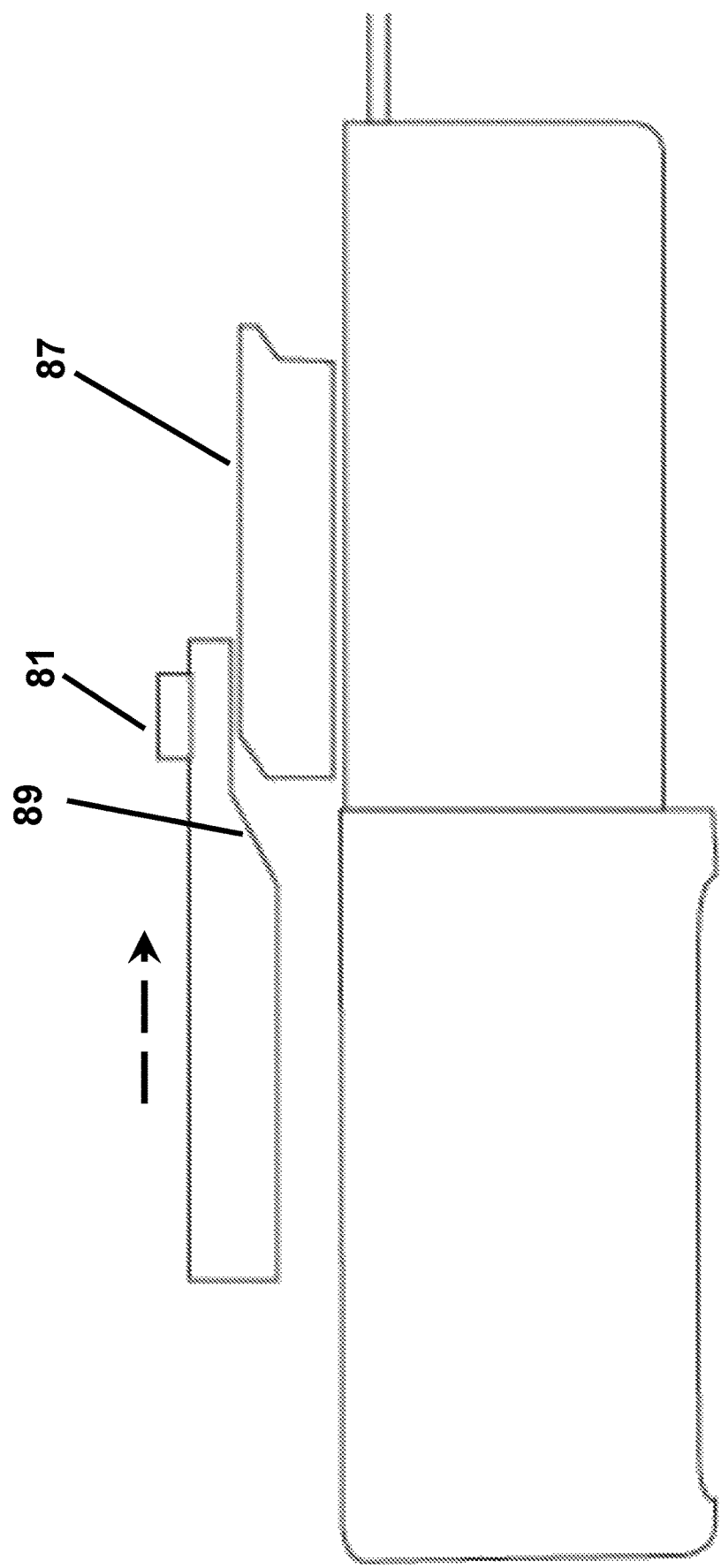
FIG. 17 is a sectioned illustration of a cartridge during actuation.
Figure 18:
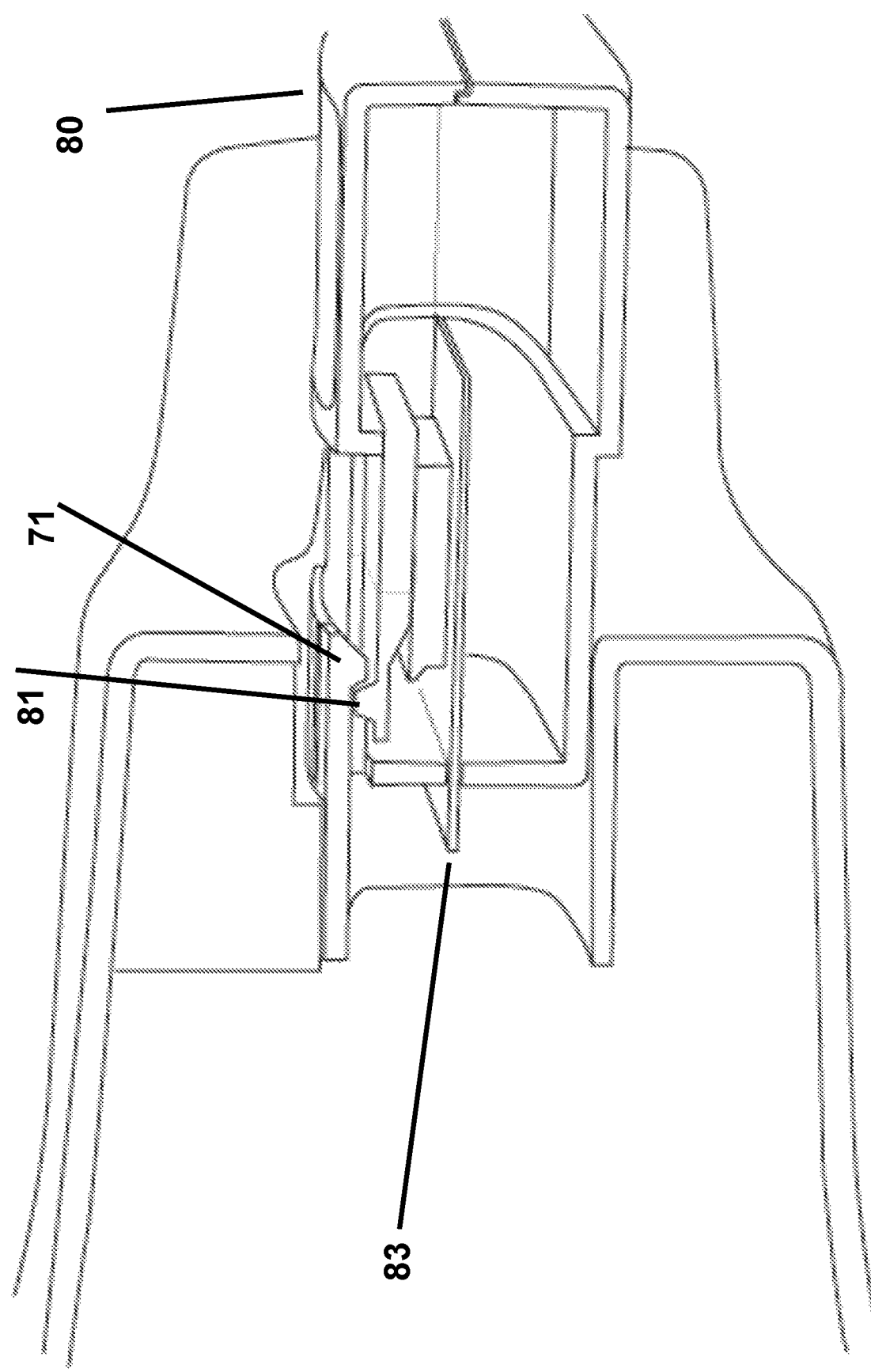
FIG. 18 is a sectioned illustration of a cartridge after actuation.

In the preferred embodiment shown in FIGS. 16-18, a sealing block 87 is shown in various states from non-sealing to sealing. The block is actuated by wedge 86 to engage the top of the microfluidic volumes 101 to seal them from fluid cross flow and fluid leakage to the outside. This isolation prevents contamination of chamber-specific reagents and reaction by-products between neighbouring chambers and also ensures electrical isolation between chambers. During sealing some fluid will be spread into unfilled chambers and some fluid will flow over the chip into overflow chambers. Alternatively, there may be no overflow chambers and instead excess fluid can collect inside the housing. In some embodiments, a skirt is provided around the sensor chip to retain fluid. The skirt may be connected to the sealing block 87 and the PCB 83 to bias the gap in the unsealed position and then flex when the block is in a sealing position.

The combination of block 87 and sensor chip 100 provide a structure for retaining a fluid, means for moving the block and sensor chip to seal and isolate chambers, an electrode providing a reference electrode, reagents exposable to each chamber, a plurality of sensors, and a connector to an analyser.

In one embodiment, a plurality of sensor types are used to determine a plurality of properties of the fluid. For example, temperature, chemiluminescense, fluorescence, pH, [Na+], [K+], and other ion concentration sensors may be used. In a second embodiment, an array of sensors of the same sensor type is used to test the fluid by reacting the sample with a different reagent or reagent mix in each chamber. So although the fluid flowing into the chambers is substantially identical, a plurality of properties can be determined by adding a plurality of analyte specific reagents (ASR) to determine whether each analyte is present. The ASRs may be sequence-specific or allele specific primers, antigen specific antibodies, or other reagent chosen to chemically react with a target in the sample.

From a knowledge of the likely constituents of a sample, such as bases of a nucleic acid, types of proteins, or molecules and the by-products (including the null by-product case) of these constituents with a given reagent, one can identify the constituent. The precision of the identity depends on the specificity of the reagent and range of likely constituents. For example, a polyclonal antibody would merely indicate whether the sample contained a member of a class of protein, whilst a monoclonal antibody could identify the specific protein. In the former case, the specific protein would be known if the sample could only contain one member of that class. Similarly a sequence specific primer would indicate whether the sample nucleic acid contained a sequence that was complementary to the primer. The sequence of interest may be a Single Nucleotide Polymorphism (SNP), in which case the primer may be an allele specific primer to identify a single base of the biological sample's nucleic acid. Monitoring of the outputs of the sensors detecting the by-products may be used to determine the difference of the change of signals between two chambers. The signal change may be the calculated as the change in signal from start to end of the reaction or in real time as the reaction progresses. The reaction may be a single reaction (nucleotide incorporation into a nucleic acid template), an on-going reaction (isothermal amplification of DNA), or a cyclical reaction (Polymerase Chain Reaction amplification of DNA). Further details can be found in patents U.S. Pat. Nos. 7,686,929 and 7,888,015 incorporated herein by reference.

Protein kinase reactions may be performed and monitored as follows. Kinases are phosphate transferring enzymes, which catalyses the transfer of the gamma phosphate of ATP to the free hydroxyl-groups of selective amino acids 131 such as serine, threonine and tyrosine; these amino acids are referred to as phosphate acceptors. The hydrolysis of ATP during the phosphate-transferring reaction leads to the release of free hydrogen ions. Substrates of protein kinases can be proteins, as well as peptides of 18-20 amino acids in length. Typically the peptides are recognised by the ability of the protein kinase active site to dock cognate substrates. Depending on the class of the protein kinase, a part of the specificity can be obtained through the sequence of amino acids surrounding the phosphate-acceptor amino acid. Thus, specific peptide sequences can be used to monitor the kinase activity in vitro.

Peptides are small fragments of proteins generally contain 18-20 amino acids in length. Peptides tend to lack the secondary and tertiary structures that collectively make up the physio-chemical properties of the corresponding protein, thus making them easier to handle.

For instance, peptides can be immobilized within each microfluidic chamber. Each individual chamber contains sequence-specific peptides that can be recognized by a particular kinase or class of kinases. Kinases can be introduced into the chambers as: cell lysates; soluble purified native or recombinant proteins; immobilized on micro beads via antibody or affinity tag that are conjugated to the micro beads. The immobilized kinases can be released via enzymatic cleavage or other alternative means.

Figure 20:
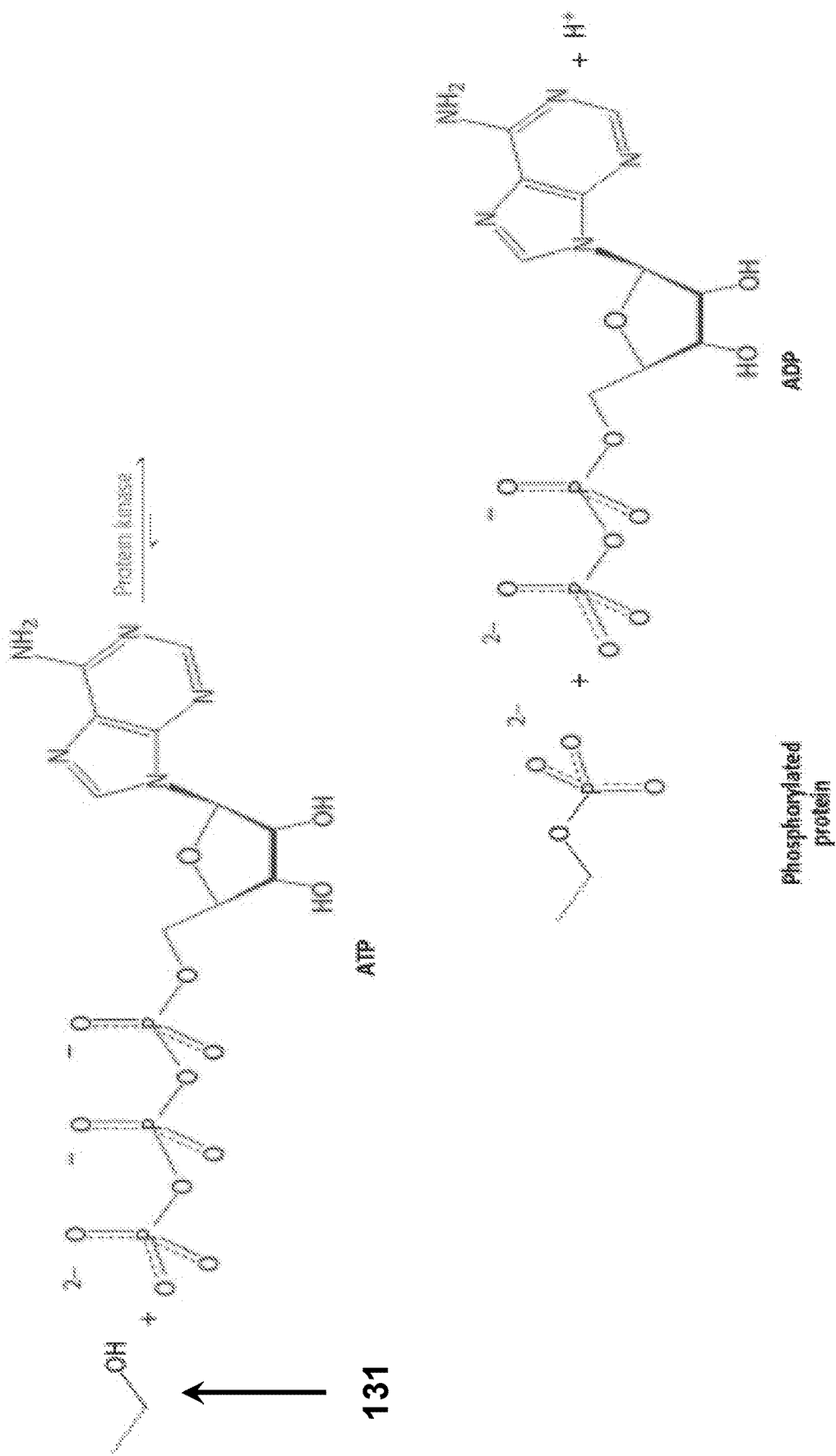
FIG. 20 is an illustration of a chemical reaction involving a protein.

To begin the reaction, the peptides are released. If the sequence surrounding the phosphate acceptor amino acid complements the corresponding kinase, a phosphorylation reaction can take place, where a phosphate, hydrolysed from an ATP, is transferred onto the peptide by the kinase. The described biochemical reaction generates a hydrogen ion by-product, which then can be detected by the sensor. The reaction is depicted in FIG. 20 (see reference Berg J M, Tymoczko J L, Stryer L, Biochemistry, 5th edition 2002).

The ASRs and other reagents may be added to each chamber before or after the adding fluid to be tested. For example the chip surface, chamber walls, or seal block may be spotted with a microliter volume containing reagents, which are then dried down for short- or long-term storage prior to use of the sensor cartridge for testing. The reagents may be spotted using commercially available deposition equipment including inkjet printers (piezo-electric or thermally actuated), screen printing and micro-dispensing pipettes. Once the fluid is sealed in a chamber and the reagents have dissolved into the fluid, a reaction takes place if the target analyte is present, whose by-products are detected by the sensor(s). The by-product may be a chemical, ion or physical property, such as heat.

After drying, the reagents may be covered by or fixed in a substance (such as wax) to be released upon melting in the fluid to be tested. Therefore one can ensure that the reaction does not happen before the fluid is separated in to chambers or the sensors are connected to a detection circuit. In the preferred system shown in FIG. 1, the sensor cartridge 80 is connected to the sample preparation device 70 to receive fluids and is then removed to be connected to the analyser 110. In a user actuated application, it will be uncertain when the user will move the cartridge so controlling the timing of the reaction is important.

The reagents may first be deposited in chambers and then covered by the substance. Alternatively the reagents may be mixed into the wax and the combination deposited into chambers.

The substance preferably has a melting point below the operating temperature of the chip and higher than the ambient temperature. The substance is preferably inert with respect to the reaction in the chamber and insoluble in the sample fluid.

A wax is a compound which is typically insoluble in water, malleable near room temperature, and melts at a relatively low temperature (e.g. above 40° C.). In preferred embodiments, the wax is substantially insoluble in the fluid provided to the volume at the initial conditions. Practically this could mean that less than 5% of the reagents dissolve into the fluid before the volume is sealed and the heater turned on. The wax may be paraffin.

Preferably there are heaters and temperature sensors within the housing connected to a controller. When the fluid has been delivered to the microfluidic volumes, sealed and isolated from each other, the controller can turn on the heater to control the timing of the reaction between reagents in the wax and the fluid. The heater and temperature sensor may be integrated in the semiconductor chip 112, PCB 116, or sealing block 87.

Microfluidics

Microfluidic chambers 101 may be provided by a thin membrane having portions removed over sensors on the semiconductor chip. The membrane provides an inexpensive layer through which holes are made to provide the sides of the chambers. The bottom of the chamber is provided by the sensor surface. The membrane comprises a surface which conforms to the sensor surface to provide sealing. The holes may be created by laser cutting, water jet, routing, drilling, or die cutting. Commercial processes exist to cut the membrane to provide volumes on the order of microlitres. In a preferred embodiment, the volume is less than 10 ul, less than 5 ul, less than 1 ul, or less than 0.2 ul. The membrane may be a pressure sensitive adhesive, a flexible PCB, a rigid PCB, a gasket with adhesive, underfil epoxy, or a sheet of BondPly which is a layer of acrylic which provides an adhesive layer when heated. The membrane may comprise a PCB to provide laminate structure 116 shown in FIG. 12.

Figure 12:
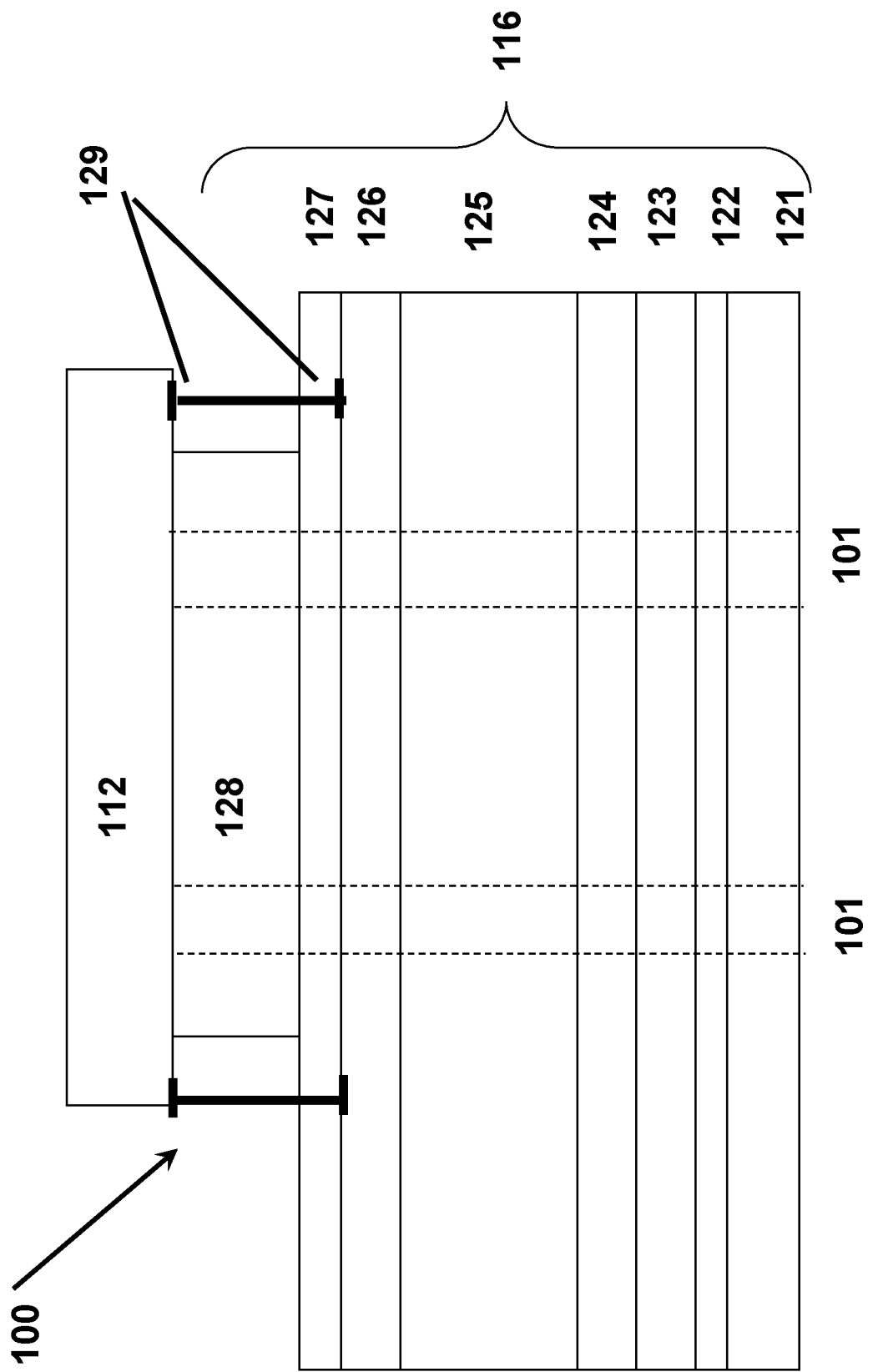
FIG. 12 is an illustration of a laminate structure comprised in a sensor chip.

As shown in the preferred embodiment of FIG. 12, the sensor chip 100 comprises a semiconductor chip 112 integrating an array of sensors, heaters, temperature sensors, control circuitry, and laminate structure 116 containing microfluidic chambers 101 overlaying the sensors. In a preferred embodiment, the sensors are Ion Sensitive Field Effect Transistors (ISFETs) which detect protons released or absorbed during a hydrolysis reaction. The semiconductor chip is preferably made in a standard CMOS process to reduce manufacturing costs and improve reliability. The laminate structure may comprise a Printed Circuit Board (PCB) which provides an electrical connection 83 between the semiconductor chip and an analyser 110. An edge of the PCB or connector on the PCB plugs into the analyser 110, providing both a mechanical and electrical connection. FIG. 12 shows a laminate structure creating a dual-sided circuit board 116 having:

- core material 125 which may be a flexible structure made of polyimide (100-150 um thick);
- cover layers 121, 123, 127 which provide insulation between neighbouring layers (20-50 um thick);
- conductive plating 124,126 which is etched to provide circuit tracks (20-50 um thick). The semiconductor chip 112 is electrically connected to the PCB by aligned bond pads 129 on the chip and a plating layer 126;
- silver/silver-chloride ink 122 which is printed to provide electrodes (1-10 um thick); and
- pressure sensitive adhesive 128 which provides a mechanical connection to the semiconductor chip with sealing between chambers (30-80 um thick).
- Portion of these layers may be selectively removed to provide the desired electrical pathways or to permit access to previous layers As a first alternative to the membrane described above, microfluidic structures may be provided directly on the semiconductor chip using MEMS techniques. Post-CMOS processing steps such as photo lithography may be used to build up layer(s) of polyimide, SU-8, and/or SiO2, the layer(s) defining microfluidic wells. Such techniques are known to persons skilled in the art, the structure, process and material choice depending on the application.

As a second alternative, a microfluidic structure may be formed as part of the sealing block. The wells may be formed during injection moulding of the block or by hot embossing or other technique suited to high volume manufacturing.

In any case, microfluidic structures are provided by the combination of sensing surface, block surface and a structure defining walls for each volume. The combination is arranged such that fluid can flow through a gap between surfaces into open wells, the combination being movable to close the gap and isolate individual reaction chambers.

Electrodes

The sensor chip comprises an electrode exposed to each chamber. In use, the electrodes provide a reference voltage to the fluid which enables the detection system to set the threshold voltage of the transistor. The electrode 92, 93, 122 may for example be silver/silver-chloride, gold, or platinum.

Figure 11:
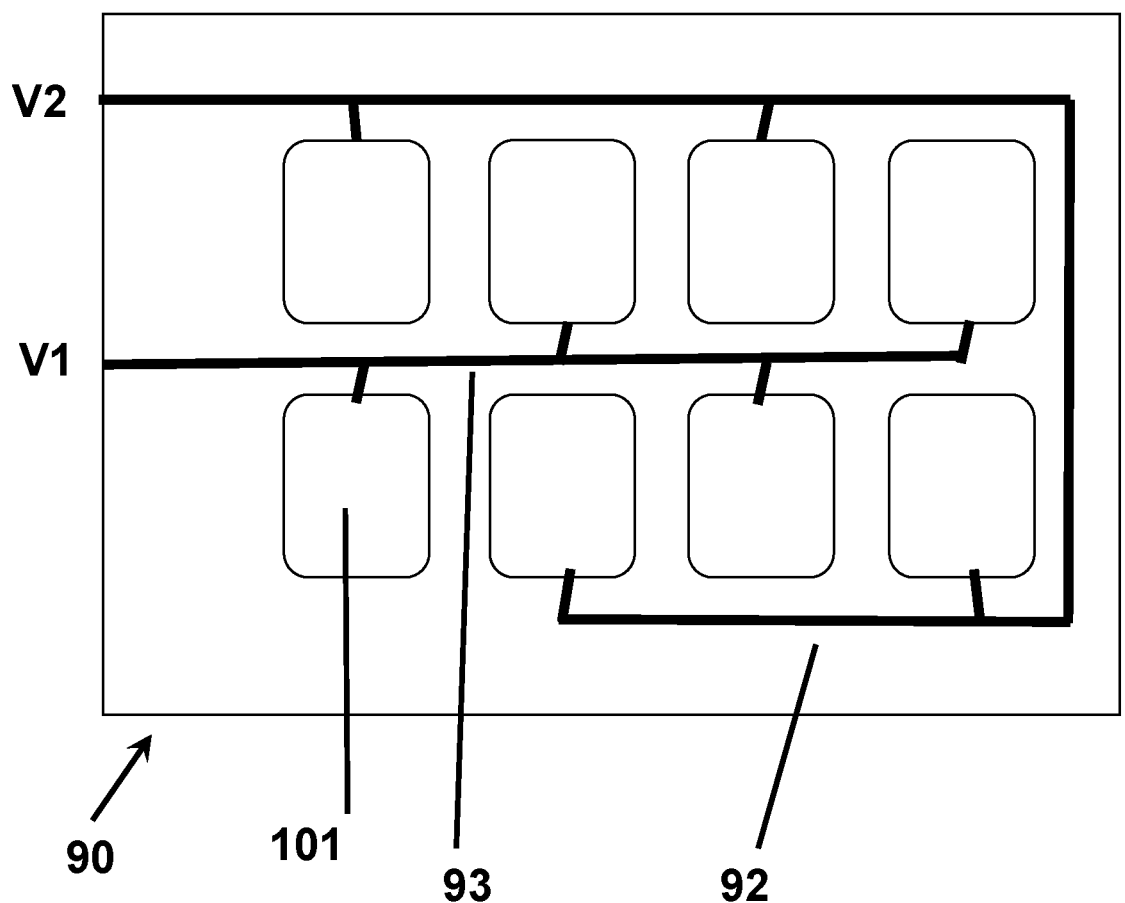
FIG. 11 is an illustration of microfluidic chambers exposed to electrodes.

The electrode 122 may be screen printed onto the sensor chip surface or onto a PCB surface coupled to the sensor chip. The electrode may be silver/silver-chloride composition 5874 from DuPont. Alternatively the electrode is provided by the circuit tracks on the PCB. FIG. 11 shows two electrode paths 92, 93 exposed to the edge of the microfluidic chambers 101. The electrode paths contact alternate chambers such that neighbouring chambers are exposed to different electrodes paths. In this way, leakage may be detected prior to testing by using different reference potentials V1, V2 for each electrode path and using sensors in each chamber to determine if the potential from a neighbouring chamber is present in a particular chamber. For example, one electrode path potential may be set to 0V and the other to 3V. Only sensors exposed to the electrodes having a potential of 3V should indicate so; detection of this potential in neighbouring chambers/sensors would indicate a fluidic leak between chambers. This error could be reported to the user, analyser 110, or external computer.

As used herein, 'external' refers to features related to but not necessarily part of the device or method being discussed or claimed.

The electrode may be part of the laminate structure 116, as shown in FIG. 12. To protect the PCB from the environment, the PCB, including electrode, is covered with cover layer 121. This has the added advantage of minimizing the area of electrode exposed to the fluid, as certain chemical reaction such as PCR are sensitive to the presence of metal. The laminate structure 116 is cut through to expose only the cross sectional area of the electrode, thus providing a reference signal with minimal surface area. Preferably the electrode is exposed during the process to create the microfluidic volumes as discussed above.

Pulling out the cartridge from the sample prep device concurrently engages a wedge to push down a cover onto the chip to isolate each chamber. FIGS. 16 to 18 show catch 81 connected to wedge 86 having a inclined surface 89 that contacts an inclined surface of block 87 such that horizontal motion of 81 results in vertical displacement of block 87 to spread the fluid across the chip from one end and seal the chambers.

FIG. 18 shows the cartridge engaged in the sample preparation device. Cantilevers 71 on the sample preparation device have hooks to flexibly contact and pull on catch 81 of the cartridge such that removal of the cartridge drags catch 81 and wedge 86 to actuate the block 87. Toward the end of travel, hooks 71 ride up on protrusions 82 to release the catch and thus cartridge.

To complete the test system, the sensor chip is connected to a power supply to run the circuits, signal processing means to monitor the sensor signals and determine a property of the sample, memory to store pre- and post-processing values, and Input/Output (I/O) circuitry to interface the device with an external processor such as a computer or instrument.

In one embodiment the sensor chip itself further comprises the signal processing circuitry, memory, and I/O circuitry.

Figure 21:
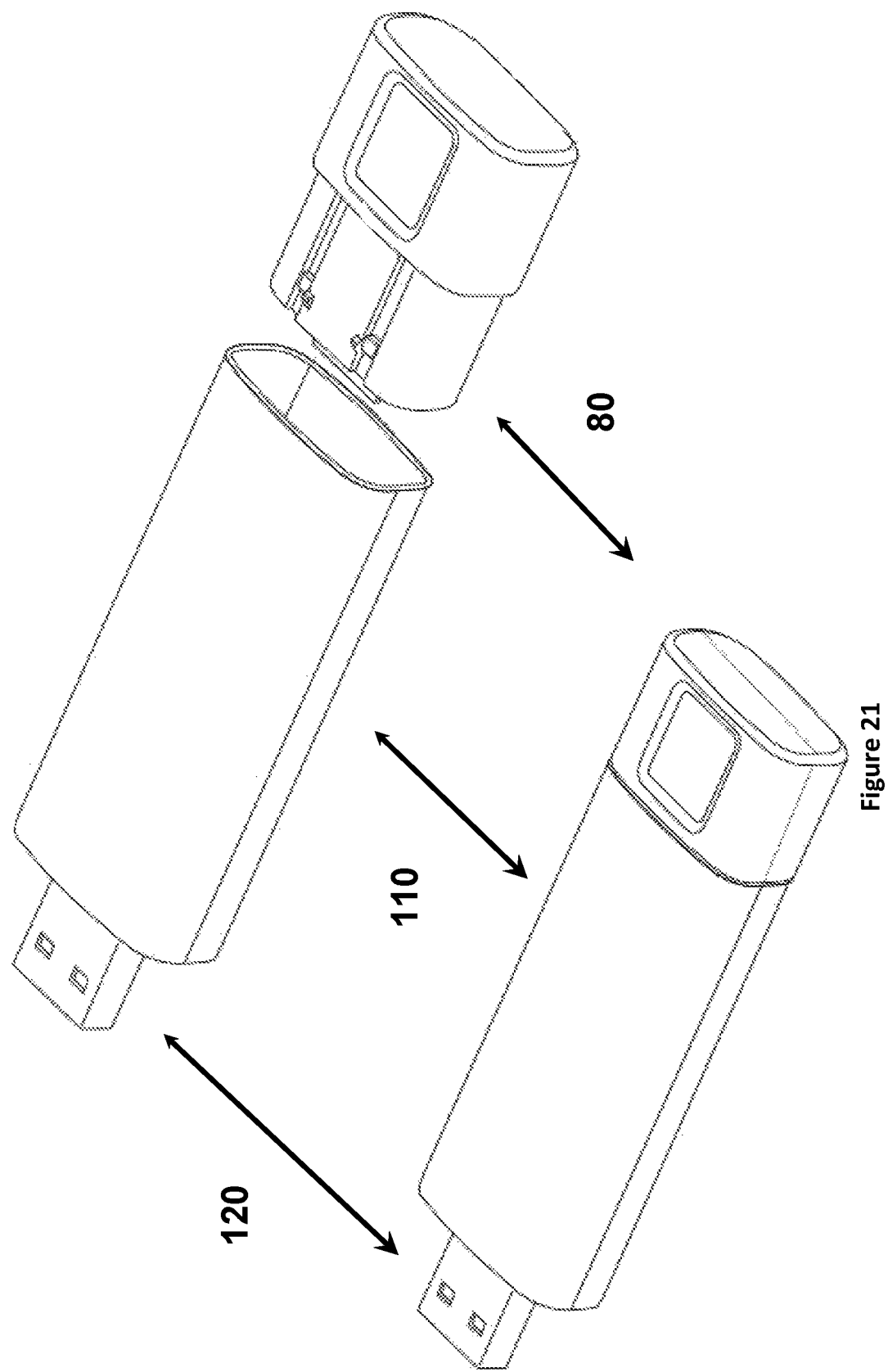
FIG. 21 is an illustration of a cartridge engaged in an analyser.

In another embodiment shown in FIG. 21, the cartridge 80 is plugged into an analyser 110, the analyser comprising a housing, and circuit for signal processing, memory, sensor interface and I/O circuitry.

In another embodiment, the cartridge itself contains its own power supply on a battery and the semiconductor chip contains a signal processor and controller.

Figure 22:
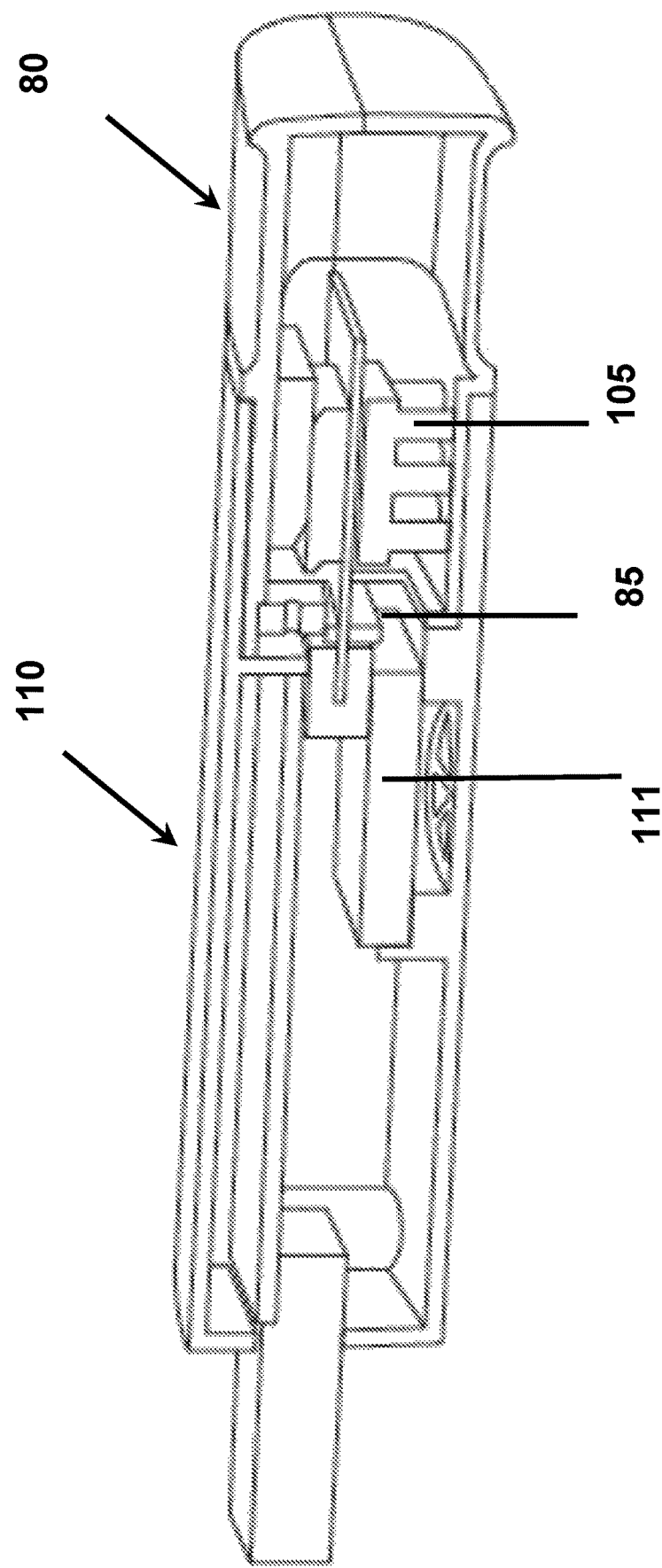
FIG. 22 is a sectioned illustration of a cartridge and analyser.

Depending upon the amount of heat generated as waste from the circuit and as part of the chemical environment (e.g. thermocycling between 95° C. and 60° C. for PCR), the temperature of the device may get too high for operation. As shown in FIG. 22, a fan 111 may be incorporated within the analyser housing to cool the device and a heat sink 105 coupled to the sensor chip to enhance dissipation. The ambient air may be drawn into the analyser housing and then directed through the port connecting the analyser and cartridge.

As an alternative, a Peltier element may be integrated into the sensor chip, powered by the analyser to accelerate heat exchange.

Contrary to current systems where fluids are manipulated and tested on a millilitre scale, embodiments of the present invention may use much smaller volumes which enable the devices to be smaller and use less reagent volume. However, simply miniaturizing known processes becomes problematic in a simple, automated, mass-manufactured product because variations in components, dead volumes, and component flexing mean that the variation in mixing would exceed the range appropriate for the reactions. The design described herein allows ease of manufacture as the plunger and cylinder can be made to macro dimensions such that strength and quality can be ensured whilst providing precise dispensing of microliters of fluid. Moreover the user does not need to be precise in their actuation, as a single action to completion is all that is required for the device to mix the correct ratios. Similarly the volume of the final mixed fluid dispensed is robustly handled by providing microfluidic wells exposed to each sensor, allowing overfill into the cartridge housing, and sealing the wells to a specified volume.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A biological sample preparation device comprising:
a housing;
a plurality of fluid dispensers located within the housing;
wherein each of the plurality of fluid dispensers comprises a cylinder and a plunger configured to stroke within the cylinder to dispense fluid, in use;
a cap coupled to the housing and movable relative to the housing;
a mechanism to translate movement of the cap into a preset combination of sequential and simultaneous movements of the plungers of the fluid dispensers, in order to mix the biological sample and reagents, said mechanism having concentric circular cam tracks on a surface connected to the cap which translate a rotating motion of the cap into sequential and simultaneous movements of the plurality of fluid dispensers, each of said concentric circular cam tracks being located at different radii from the center of the cap;
a microfluidic channel configured to communicate with the plurality of fluid dispensers and provide mixing; and
a ratchet disposed between the cap and the housing.

2. The biological sample preparation device according to claim 1, further comprising a channel, reservoir and exit slot configured to provide a smooth, precisely timed reagent flow.

3. The biological sample preparation device according to claim 1, wherein each of the plungers in the plurality of fluid dispensers are arranged to move concurrently to dispense separate fluids.

* * * * *